(12) United States Patent
McDevitt et al.

(10) Patent No.: US 6,339,064 B1
(45) Date of Patent: Jan. 15, 2002

(54) BENZYLGLYCOSYLAMIDES AS INHIBITORS OF SMOOTH MUSCLE CELL PROLIFERATION

(75) Inventors: Robert E. McDevitt, Somerset; Folake O. Adebayo, Cranbury, both of NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/447,004

(22) Filed: Nov. 22, 1999

Related U.S. Application Data
(60) Provisional application No. 60/126,440, filed on Nov. 24, 1998.

(51) Int. Cl.[7] .................. A61K 31/70; A61K 31/715; C07H 5/06

(52) U.S. Cl. .................. 514/42; 514/53; 536/29.1; 536/29.11; 536/29.13

(58) Field of Search .................. 536/29.1, 29.11, 536/29.13; 514/42, 53

(56) References Cited

U.S. PATENT DOCUMENTS

| | | | |
|---|---|---|---|
| 2,752,334 A | 6/1956 | Walton | 260/211 |
| 4,431,637 A | 2/1984 | Upeslacis et al. | 424/180 |
| 5,019,562 A | 5/1991 | Folkman et al. | 514/58 |
| 5,037,973 A | 8/1991 | Meinetsberger | 536/3 |
| 5,296,588 A | 3/1994 | Au et al. | 536/1.11 |
| 5,310,542 A | 5/1994 | Au et al. | 424/52 |
| 5,326,752 A * | 7/1994 | Nashed et al. | 514/25 |
| 5,336,765 A | 8/1994 | Au et al. | 536/18.5 |
| 5,447,919 A * | 9/1995 | Hosang et al. | 514/53 |
| 5,464,827 A | 11/1995 | Soll | 514/58 |
| 5,498,775 A | 5/1996 | Novak et al. | 514/25 |

FOREIGN PATENT DOCUMENTS

| | | |
|---|---|---|
| EP | 0312086 | 4/1989 |
| EP | 0312087 | 4/1989 |
| EP | 0356275 | 2/1990 |
| EP | 0454220 | 10/1991 |
| EP | 0550106 | 7/1993 |
| EP | 0551675 | 7/1993 |
| EP | 0714903 | 6/1996 |
| JP | 0730478 | 11/1995 |
| WO | 9006755 | 6/1990 |
| WO | 9309790 | 5/1993 |
| WO | 9614324 | 5/1996 |
| WO | 9614325 | 5/1996 |
| WO | 0031094 | 6/2000 |

OTHER PUBLICATIONS

Defarrari, Jorge O. et al: "The reaction of ammonia with acylated disaccharides Part X. Octa–O–benzoyl–lactose and other benzoyl derivatives of lactose" *Carbohyd. Res.* (1973), 29 (1), 141–6.

Ng, Ken et al: "Specificity of binding of β–glusocide activators of ryegrass (1–3)–β–glucan synthase and the synthesis of some potential photoaffinity activators" *Plant Physiol.* (1996), 111(4), 1227–1231.

Zehavi, Carbohyd. Res., 1986, 151,371.

(List continued on next page.)

*Primary Examiner*—Kathleen K. Fonda
*Assistant Examiner*—Leigh C. Maier
(74) *Attorney, Agent, or Firm*—Michael R. Nagy

(57) ABSTRACT

This invention provides smooth muscle cell proliferation inhibitors of formula I having the structure

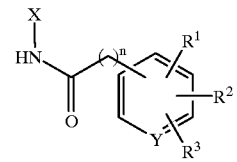

I wherein
Y is C or N;
where n is 0–3;
X is

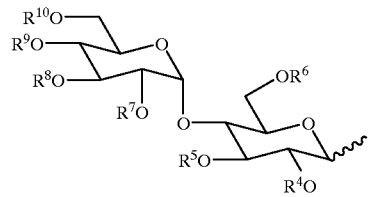

$R^1$, and $R^2$ are independently, hydrogen, alkyl of 1 to 6 carbon atoms, or halo, acetyl, phenyl, $CF_3$, CN, OH, $NO_2$, $NH_2$, alkoxy of 1 to 6 carbon atoms, or cyanoalkoxy of 2 to 7 carbon atoms;

$R^3$ is hydrogen, acylamide of 2 to 6 carbon atoms or alkoxy of 1 to 6 carbon atoms;

$R^4$, $R^5$, $R^6$, $R^7$, and $R^8$ are each, independently, acyl of 1 to 6 carbon atoms, benzyl substituted with $R^1$, and $R^2$; or benzoyl substituted with $R^1$ and $R^2$;

$R^9$ and $R^{10}$ are each, independently, acyl of 1 to 6 carbon atoms, or the $R^9$ and $R^{10}$ groups on the 4' and 6' positions of the maltose may be taken together to form a cyclic acetal which may be substituted with alkyl of 1 to 6 carbon atoms, two alkyl groups each having 1 to 6 carbon atoms, pyridine substituted with $R^1$, phenyl substituted with $R^1$, benzyl substituted with $R^1$, 2-phenylethyl substituted with $R^1$, or 3-phenylpropyl substituted with $R^1$;

with the proviso that when $R^1$ or $R^2$ are cyanoalkoxy of 2–7 carbon atoms, $R^3$ is not acylamide, and further provided that when $R^1$, $R^2$, or $R^3$ are alkoxy of 1–6 carbon atoms, at least one of $R^1$, $R^2$, $R^3$, or $R^4$ are not hydrogen;

or a pharmaceutically acceptable salt thereof.

19 Claims, No Drawings

OTHER PUBLICATIONS

Reilly et al., Drug Development Research, 1993, 29, 137.
Klein et al., Liebigs Ann. Chem., 1987, 485–489.
Durette et al., Carbohydrate Research, 1978, 67, 484–490.
Bertho, Liebigs Ann. Chem., 1949, 562, 229–239.
Kopper et al., Carbohydrate Research, 1989, 193, 296–302.
Zehavi et al., Carbohydrate Research, 1983, 124, 23–34.
Zehavi et al., Carbohydrate Research, 1992, 228, 255–263.
Connors et al., Herba Polonica, 1998, 44, 33–38.
Morales et al., Angew. Chem. Int. Ed., 1988, 37 (5), 654–657.

* cited by examiner

BENZYLGLYCOSYLAMIDES AS INHIBITORS OF SMOOTH MUSCLE CELL PROLIFERATION

This application claims the benefit of U.S. Provisional Application No. 60/126,440, which was converted from U.S. patent application Ser. No. 09/198,433, filed Nov. 24, 1998, pursuant to a petition filed under 37 C.F.R. 1.53(c)(2)(i).

BACKGROUND OF THE INVENTION

This invention relates to the use of substituted benzylglycosylamides as smooth muscle cell proliferation inhibitors and as therapeutic compositions for treating diseases and conditions which are characterized by excessive smooth muscle proliferation such as restenosis.

All forms of vascular reconstruction such as angioplasty and vein bypass procedures effect a response to injury that ultimately leads to smooth muscle cell (SMC) proliferation and subsequently, deposition of profuse amounts of extracellular matrix (Clowes, A. W.; Reidy, M. A. *J. Vasc. Surg* 1991, 13, 885). These events are also central processes in the pathogenesis of atherosclerosis (Raines E. W.; Ross R. *Br. Heart J.* 1993, 69 (Supplement), S. 30) as well as transplant arteriosclerosis (Isik, F. F.; McDonald, T. O.; Ferguson, M.; Yamanaka, E.; Gordon *Am. J. Pathol.* 1992, 141, 1139). In the case of restenosis following angioplasty, clinically relevant solutions for controlling SMC proliferation through pharmacological intervention have remained elusive to date (Herrman, J. P. R.; Hermans, W. R. M.; Vos, J.; Serruys P. W. *Drugs* 1993, 4, 18 and 249). Any successful approach to selective SMC proliferation inhibition must not interfere with endothelial cell repair or the normal proliferation and function of other cells (Weissberg, P. L.; Grainger, D. J.; Shanahan C. M.; Metcalfe, J. C. *Cardiovascular Res.* 1993, 27, 1191).

The glycosaminoglycans heparin and heparan sulfate are endogenous inhibitors of SMC proliferation, yet are able to promote endothelial cell growth (Castellot, J. J. Jr.; Wright, T. C.; Karnovsky, M. J. *Seminars in Thrombosis and Hemostasis* 1987, 13, 489). However, the full clinical benefits of heparin, heparin fragments, chemically modified heparin, low molecular weight heparins, and other heparin mimicking anionic polysaccharides may be compromised due to other pharmacological liabilities (excessive bleeding arising from anticoagulation effects, in particular) coupled with heterogeneity of the various preparations (Borman, S. *Chemical and Engineering News,* 1993, Jun. 28, 27).

WO 96/14325 discloses acylated benzylglycosides as smooth muscle cell proliferation inhibitors. The compounds of the present invention differ in that (a) the carbohydrate posesses an anomeric amide, (b) the substituents on the carbohydrate backbone are substantually different and, (c) the activity against smooth muscle cell proliferation is greater.

Zehavi, U., in *Carbohyd. Res.* 1986, 151, 371, disclosed 4-carboxy-2-nitrobenzyl 4-O-α-D-glucopyranosyl-β-D-glucopyranoside which is attached to a polymer for study as an acceptor in the glycogen synthase reaction. The compounds of the present invention differ in that (a) the carbohydrate posesses an anomeric amide, (b) the substituents on the benzyl groups are different and (c) the use (smooth muscle antiproliferation) is different.

U.S. Pat. No. 5,498,775, WO96/14324, and U.S. Pat. No. 5,464,827 describe polyanionic benzylglycosides or cyclodextrins as smooth muscle cell proliferation inhibitors for treating diseases and conditions which are characterized by excessive smooth muscle proliferation. β-cyclodextrin tetradecasulfate has been described as a smooth muscle cell proliferation inhibitor and as an effective inhibitor of restenosis (Reilly, C. F.; Fujita, T.; McFall, R. C.; Stabilito, I. I.; Wai-se E.; Johnson, R. G. *Drug Development Research* 1993, 29, 137). U.S. Pat. No. 5,019,562 discloses anionic derivatives of cyclodextrins for treating pathological conditions associated with undesirable cell or tissue growth. WO 93/09790 discloses antiproliferative polyanionic derivatives of cyclodextrins bearing at least 2 anionic residues per carbohydrate residues. Meinetsberger (EP 312087 A2 and EP 312086 A2) describes the antithrombotic and anticoagulant properties of sulfated bis-aldonic acid amides. U.S. Pat. No. 4,431,637 discloses polysulfated phenolic glycosides as modulators of the complement system. The compounds of the present invention differ from all of the prior art in that the compounds (a) are benzylglycosylamides which bear no structural resemblance to heparin, sulfated cyclodextrins, or to sulfated lactobionic acid dimers, (b) contain no more than two contiguous sugar residues (disaccharide), (c) are of a defined structure, (d) and are not sulfated.

DESCRIPTION OF THE INVENTION

This invention provides benzylglycosylamides of formula I

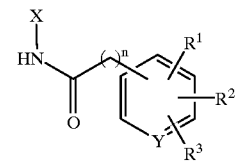

wherein
Y is C or N;
where n is 0–3;
X is

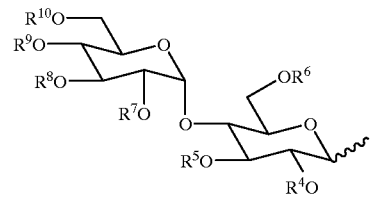

$R^1$, and $R^2$ are each independently, hydrogen, alkyl of 1 to 6 carbon atoms, halo, acetyl, phenyl, $CF_3$, CN, OH, $NO_2$, $NH_2$, alkoxy of 1 to 6 carbon atoms, or cyanoalkoxy of 2 to 7 carbon atoms;

$R^3$ is hydrogen, acylamide of 2 to 6 carbon atoms or alkoxy of 1 to 6 carbon atoms;

$R^4$, $R^5$, $R^6$, $R^7$, and $R^8$ are each, independently, acyl of 1 to 6 carbon atoms, benzyl substituted with $R^1$, and $R^2$; or benzoyl substituted with $R^1$ and $R^2$;

$R^9$ and $R^{10}$ are each, independently, acyl of 1 to 6 carbon atoms, or the $R^9$ and $R^{10}$ groups on the 4' and 6' positions of the maltose may be taken together to form a cyclic acetal which may be substituted with alkyl of 1 to 6 carbon atoms, two alkyl groups each having 1 to 6 carbon atoms, pyridine substituted with $R^1$, phenyl substituted with $R^1$, benzyl substituted with $R^1$, 2-phenylethyl substituted with $R^1$, or 3-phenylpropyl substituted with $R^1$;

with the provisio that when $R^1$ or $R^2$ are cyanoalkoxy of 2–7 carbon atoms, $R^3$ is not acylamide, and further provided that when $R^1$, $R^2$, or $R^3$ are alkoxy of 1–6 carbon atoms, at least one of $R^1$, $R^2$, $R^3$, or $R^4$ are not hydrogen;

or a pharmaceutically acceptable salt thereof.

Alkyl includes both straight chain as well as branched moieties. Halogen means bromine, chlorine, fluorine, and iodine. When Y is nitrogen, it is preferred that the pyridine carboxamide is pyridine 3-carboxamide.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from organic and inorganic bases, preferably alkali metal salts, for example, sodium, lithium, or potassium. Acid addition salts can be prepared when Y is nitrogen or the compound of formula I contains a basic nitrogen, and base addition salts can typically be prepared when the compound of formula I contains a hydroxyl group.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

Preferred compounds formula I of this invention are those in which n is 0–1;

$R^1$, and $R^2$ are each independently, hydrogen, halogen, $CF_3$, OH, $NO_2$, $NH_2$, methoxy, butoxy, or butoxynitrile;

$R^3$ is hydrogen, acetamide, or methoxy;

$R^4$, $R^5$, $R^6$, $R^7$, and $R^8$ are each, independently, hydrogen, an acyl of 1–6 carbon atoms, or benzoyl;

$R^9$ and $R^{10}$ are each, independently, acyl of 1–6 carbon atoms, or the $R^9$ and $R^{10}$ groups on the 4' and 6' positions of the maltose are taken together form a benzylidene ring;

or a pharmaceutically acceptable salt thereof, with all other substituents as defined above.

More preferred compounds of formula I are those in which n is 0;

$R^1$, and $R^2$ are each independently, hydrogen or halogen;

$R^3$ is hydrogen;

$R^4$, $R^5$, $R^6$, $R^7$, and $R^8$ are each, independently, hydrogen, acyl of 1 to 6 carbon atoms, or benzoyl;

$R^9$ and $R^{10}$ are each, independently, acyl of 1–6 carbon atoms, or the $R^9$ and $R^{10}$ group on the 4' and 6' positions of the maltose are taken together form a benzylidene ring;

or a pharmaceutically acceptable salt thereof, with all other substituents as defined above.

Specifically preferred compounds of this invention are:

N-(Hepta-O-acetyl-1-deoxy-β-D-maltosyl)-4-chloro-3-nitro-benzamide;

3-Amino-4-chloro-N-[2,3,6-tri-O-acetyl-4-O-(2,3,4,6-tetra-O-acetyl-α-D-glucopyranosyl)-β-D-glucopyranosyl}-benzamide;

3-(Acetylamino)-4-chloro-N-[2,3,6-tri-O-acetyl-4-O-(2,3,4,6-tetra-O-acetyl-α-D-glucopyranosyl)-β-D-glucopyranosyl}-benzamide;

(R)-3-(Acetylamino)-4-chloro-N-[4-O-[4,6-O-(phenylmethylene)-α-D-glucopyranosyl]-β-D-glucopyranosyl]-benzamide;

(R)-4-chloro-3-nitro-N-[4-O-[4,6-O-(phenylmethylene)-α-D-glucopyranosyl]-β-D-glucopyranosyl]-benzamide;

(R)-3-(Acetylamino)-N-[6-O-benzoyl-4-O-[4,6-O-(phenylmethylene)-α-D-glucopyranosyl]-β-D-glucopyranosyl]-4-chlorobenzamide;

(R)-N-[2-O-Acetyl-4-O-[2-O-acetyl-4,6-O-(phenyl methylene)-α-D-glucopyranosyl]-6-O-benzoyl-β-D-glucopyranosyl]-3-(acetylamino)-4-chlorobenzamide;

(R)-4-chloro-N-[(6-O-benzoyl-4',6'-O-benzylidene)-β-D-maltosyl]-3-nitro-benzamide;

4-Chloro-N-[(2,2',3,3'-tetra-O-acetyl-6-benzoyl-4',6'-O benzylidene)-β-D-maltosyl]-3-nitro-benzamide;

N-(Hepta-O-acetyl-β-D-maltosyl)-4-chloro-benzamide;

N-(4',6'-O-Benzylidene-β-D-maltosyl)-4-chloro-benzamide;

N-(6-O-benzoyl-4',6'-O-benzylidene-β-D-maltosyl)-4-chloro-benzamide;

N-[(2,2',3,3'4',6,6'-hepta-O-acetyl-β-D-maltosyl]-3-chloro-4-nitrilobutoxy-benzoic acid amide;

N-[(2,2',3,3'4',6,6'-hepta-O-acetyl,-α-D-maltosyl]-3-chloro-4-nitrilobutoxy-benzoic acid amide;

N-(4',6'-O-Benzylidene-β-D-maltosyl)-3-chloro-4-(4-nitrilo-butoxy)-benzamide;

N-(6-O-Benzoyl-4',6'-O-benzylidene-β-D-maltosyl)-3-chloro-4-(4-nitrilo-butoxy)-phenyl amide;

N-(2,2',3,3'-tetra-O-Acetyl-6-O-benzoyl-4',6'-O-benzylidene-β-D-maltosyl)-3-chloro-4-(4-nitrilo-butoxy)-benzamide;

4-Butoxy-3-chloro-N-[2,3,6-tri-O-acetyl-4-O-(2,3,4,6-tetra-O-acetyl-α-D-glucopyranosyl)-β-D-glucopyranosyl]benzamide;

4-Butoxy-3-chloro-N-[(6-O-benzoyl-4',6'-O-benzylidene)-β-D-maltosyl]-benzamide;

4-Butoxy-3-chloro-N-[(2,3,2',3'-tetra-O-acetyl-6-O-benzoyl-4',6'-O-benzylidene)-β-D-maltosyl]-benzamide;

4-Chloro-3-methoxy-N-[2,3,6-tri-O-acetyl-4-O-(2,3,4,6-tetra-O-acetyl-α-D-glucopyranosyl )-β-D-glucopyranosyl]benzamide;

N-(6-O-Benzoyl-4',6'-O-benzylidene-β-D-maltosyl)-4-chloro-3-methoxy-benzamide;

N-(2,2',3,3',4,6,6'-hepta-O-acetyl-β-D-maltosyl]-4-butoxy-5-chloro-3-methoxy-benzamide;

N[(6-O-benzoyloxy-4',6'-O-benzylidene)-β-D-maltosyl]-4-butoxy-3-chloro-5-methoxy-benzamide;

N-[(2,2',3,3'4',6,6'-hepta-O-acetyl-β-D-maltosyl]4-(4-nitrilo-butoxy)-3-nitro-benzamide;

N-(4',6'-O-Benzylidene-β-D-maltosyl)-4-(4-nitrilo-butoxy)-3-nitro-benzamide;

N-(6-O-Benzoyl-4',6'-O-benzylidene-β-D-maltosyl)-4-(4-nitrilo-butoxy)-3-nitro-benzamide;

N-(2,2',3,3'-tetra-O-Acetyl-6-O-benzoyl-4',6'-O-benzylidene-β-D-maltosyl)-4-(4-nitrilo-butoxy)-3-nitro-benzamide;

N-[(2,2',3,3'4',6,6'-hepta-O-acetyl-β-D-maltosyl]-3-amino-4-(4-nitrilo-butoxy)-benzamide;

3-Acetylamino-N-(6-O-benzoyl-4',6'-O-benzylidene-β-D-maltosyl)-4-(4-nitrilo-butoxy)-benzamide;

N-[(2,2',3,3'4',6,6'-Hepta-O-acetyl-β-D-maltosyl]-6-chloropyridine-3-carboxamide;

N-(Hepta-O-acetyl-β-D-maltosyl )-2,6-dimethoxy-pyridine-3-carboxamide;
N-(Hepta-O-acetyl-β-D-maltosyl )-5-bromopyridine-3-carboxamide;
N-(Hepta-O-acetyl-Oβ-D-maltosyl)-3-(trifluoromethyl)-benzamide;
N-(4',6'-O-Benzylidene-β-D-maltosyl)-3-(trifluoromethyl)-Benzamide;
N-[{6-O-Benzoyl-4',6'-O-benzylidene}-β-D-maltosyl]-3-(trifluoromethyl)-benzamide;
N-(Hepta-O-acetyl-β-D-maltosyl)-6-methylpyridine-3-carboxamide;
N-(2,9',3,3',4',6,6'-Hepta-O-acetyl-β-maltosyl)-4-butoxy-3,5-dichloro-benzylamide;
N-(4',6'-O-Benzylidene-β-D-maltosyl)-4-butoxy-3,5-dichloro-benzamide;
N-(Hepta-O-acetyl-β-D-maltosyl)-3-chloro-4-methoxy-benzamide;
N-(2,2',3,3',4',6,6'-hepta-O-acetyl-β-D-maltosyl)-1-(3,4-dimethoxy)-phenyl-acetamide;
N-(6-O-Benzoyl-4',6'-O-benzylidene-β-D-maltosyl)-2-(3,4-dimethoxy-phenyl)-acetamide;
N-(Hepta-O-acetyl-β-D-maltosyl )-2-(4-hydroxy-3-nitro-phenyl)-acetamide;
N-(2,2',3,3',4',6,6'-hepta-O-acetyl-β-D-maltosyl)-2-(4-chloro-3-nitro-phenyl)-acetamide;
2-[3-Acetyl-amino)-4-chloro-phenyl]-N-(6-O-benzoyl-4',6'-O-benzylidene-β-D-maltosyl)-acetamide;

or pharmaceutically acceptable salts thereof.

The compounds of this invention were be prepared according to the following, scheme from commercially available starting materials or starting materials which can be prepared using literature procedures. This scheme shows the preparation of representative compounds of this invention.

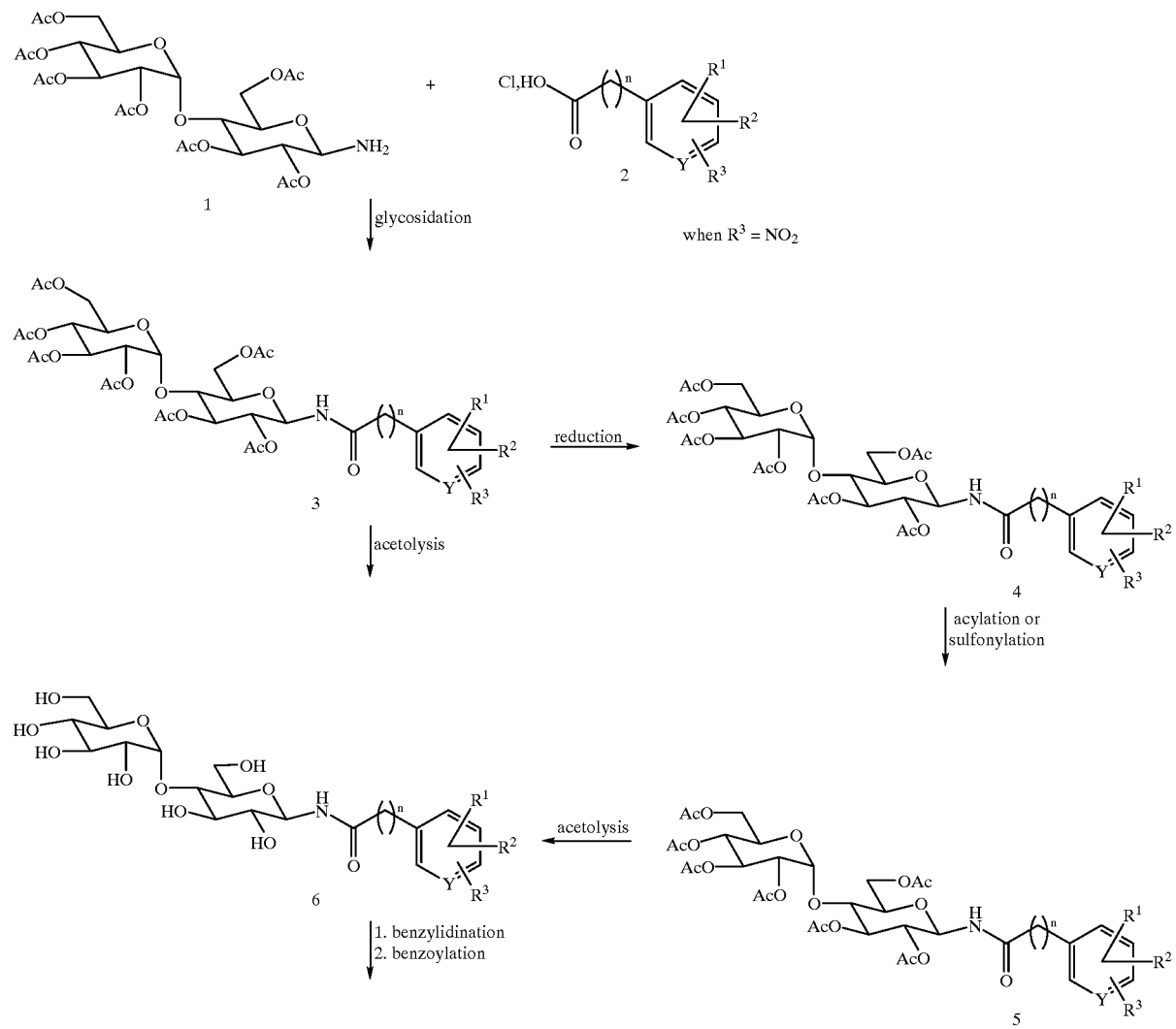

Scheme 1

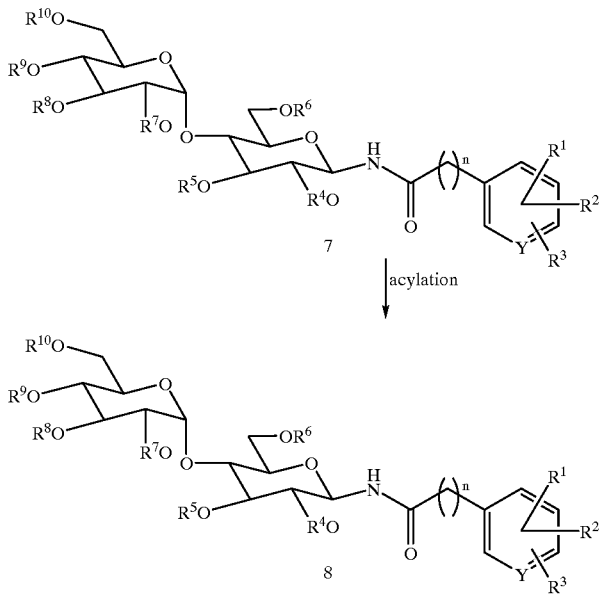

In Scheme I, Y, n, $R^1$, $R^2$, $R^3$, $R^4$, $R^5$, $R^6$, $R^7$, $R^8$, $R^9$, and $R^{10}$ are as defined above.

Thus, the maltosyl amine 1 is coupled with a benzoic acid derivative 2 in the presence of a coupling reagent such as EEDQ, DEC/HOBT, or DCC/HOBT in a suitable solvent system such as benzene, ethanol, dichloromethane, triethyl amine at room temperatures to yield glycoside 3. The glycoside can also be prepared by coupling the amine 1 to a substituted acid chloride 2 in the presence of triethyl amine in a suitable solvent system such as tetrahydofuran, dichloromethane, acetonitrile, and ethyl acetate to yield glycoside 3. When $R^3$ equals a nitro group reduction of the nitro group of 3 can be accomplished with a reducing agent such as stannous chloride or iron metal in a polar aprotic solvent such as ethyl acetate or a polar protic solvent such as ethanol or methanol at ambient temperature to reflux, or by catalytic hydrogenation in the presence of a catalyst such as palladium on carbon gives in anilino compound 4. Coupling of 4 with an acid chloride or sulfonyl chloride in the presence of an amine base such as triethylamine or diisopropulethlylamine in an aprotic solvent such as dichloromethane or tetrahydrofuran at temperatures ranging from −20° C. to ambient temperature yields the target compounds 5.

The acetate groups of 3 or 5 can be removed by hydrolysis with a base such as catalytic sodium methoxide in methanol or aqueous sodium hydroxide in methanol at ambient temperature to reflux to yield 6. After hydrolysis of the acetate groups, the 4' and 6' hydroxy groups of maltose can be reacted with benzaldehyde diemthyl acetal in the presence of an acid catalyst such as camphorsulfonic acid or toluene sulfonic acid in a polar aprotic solvent such as acetonitrile or dimethyl formamide at ambient temperature to 70° C. to yield a benzylidene derivative. The 6 hydroxyl group can be selectively benzoylated in a collidine/tetrahydofuran mixture at −78° C. to ambient temperature to yield 7. Reacylation with an acyl anhydride in the presence of an amine base such as pyridine or triethyl amine at temperatures ranging from 0° C. to ambient temperature to yield 8.

The compounds of this invention are useful as antiproliferative agents. The following procedures show the evaluation of representative compounds of this invention in standard pharmacological test procedure which measured ability of the evaluated compound to inhibit smooth muscle cell proliferation.

Effects of Compounds on Cell Proliferation Using $^3$H Thymidine Incorporation

Human and porcine smooth muscle cells were tested in early passage (generally passage 3–7) at sub-confluent conditions. Cultures were grown in 16 mm (24 well) multi-well culture dishes in medium 199 supplemented with 10% fetal bovine serum and 2% antibiotic/antimycotic. At sub-confluence, the cells were placed in a defined serum free medium (AIM-V; Gibco) for 24–48 h prior to initiating the experimental protocol.

Although compounds were found to be more effective with longer pre-incubations, in general, the procedures were initiated with the addition of compound, $^3$H thymidine and serum/growth factor to serum deprived synchronized cells and results are reported accordingly.

Compounds were added to each well at 50 fold dilution (20 μL/well) and the plates were incubated for 24–36 h at 37° C. in 5% $CO_2$. Compounds were initially dissolved in 50% ethanol and serially diluted into media. Compounds were routinely evaluated at concentrations from 1 to 100 μM. As a control, grade II porcine intestinal mucosal herapin (sodium salt) was routinely evaluated in all cell preparations at concentrations from 0.1 to 100 μg/mL.

At the completion of the test procedure, plates were placed on ice, washed three times with ice cold phosphate buffered saline (PBS) and incubated in ice cold 10% trichloroacetic acid (TCA) got 30 min to remove acid soluble proteins. Solution was transferred to scintillation vials containing 0.4 N HCl (500 μL/vial to neutralize NaOH) and each well was rinsed two times with water (500 μL) for a total volume of 2 mL/vial.

Data was obtained, in triplicate, for both control and experimental samples. Control (100%) data was obtained from maximally stimulated cells, as the result of growth factor or serum stimulation. Experimental data was obtained from cells maximally stimulated with growth factor or serum and treated with compound. Data are expressed as an $IC_{50}$ in Table I below.

TABLE 1

| Compound of Example | Porcine Smooth Muscle Cell Antiproliferation IC50 |
| --- | --- |
| 1 | 21.2 μM |
| 2 | 11.13 μM |
| 3 | 54.3 μM |
| 4 | 3.2 μM |
| 5 | 37% at 50 μM |
| 6 | 0.45 μM |
| 7 | 0.55 μM |
| 8 | 0.26 μM |
| 9 | 1.253 μM |
| 10 | 36.6 μM |
| 11 | 15% at 50 μM |
| 12 | 49.2 μM |
| 13 | 32.8 μM |
| 14 | 51.3 μM |
| 15 | 30% at 50 μM |
| 16 | 0.27 μM |
| 17 | 33% at 50 μM |
| 18 | 3.5 μM |
| 19 | 35% at 50 μM |
| 20 | 3.14 μM |
| 21 | 9.8 μM |
| 22 | 18.5 μM |
| 23 | 2% at 50 μM |
| 24 | 2.0 μM |
| 25 | 2.7 μM |
| 26 | 32% at 50 μM |
| 27 | 45% at 50 μM |
| 28 | 3% at 50 μM |
| 29 | 4% at 50 μM |
| 30 | 1.4 μM |
| 31 | 15% at 50 μM |
| 32 | 10% at 50 μM |
| 33 | 0% at 50 μM |
| 34 | 0.98 μM |
| 35 | 66.6 μM |
| 36 | 13.6 μM |
| 37 | 16.4 μM |
| 38 | 5.8 μM |
| 39 | 15% at 50 μM |
| 40 | 7.15 μM |
| 41 | 65.77 μM |
| 42 | 28.9 μM |
| 43 | 44.5 μM |
| 44 | 5.4 μM |
| 45 | 16.6 μM |
| 46 | 0% at 50 μM |
| 47 | 8.0 μM |
| 48 | 37% at 50 μM |
| 49 | 12.6 μM |
| 50 | 4.23 μM |
| 51 | 0.916 μM |

The compounds of this invention are useful in treating or inhibiting diseases which are characterized by excessive smooth muscle cell proliferation (smooth muscle cell hyperproliferation). The compounds are particularly useful in treating hyperproliferative vascular diseases which are characterized by smooth muscle cell hyperproliferation, such as restenosis, which most frequently arises from vascular reconstructive surgery and transplantation, for example, balloon angioplasty, vascular graft surgery, coronary artery bypass surgery, and heart transplantation. Other disease states in which there is unwanted "cellular" vascular proliferation induce hypertension, asthma, and congestive heart failure. The compounds of this invention are also useful as inhibitors of angiogenesis. Angiogenesis (neovascularization), the process by which new capillaries are formed, is of principal importance for a number of pathological events including chronic inflammation and malignant processes. The compounds of this invention are therefore useful as antineoplastic agents.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymetlhyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.1 to 10 mg/kg administered parenterally (intravenous preferred), with projected daily oral dosage being approximately ten-fold higher. Anticipated intravenous administration would last for approximately 5–30 days following acute vascular injury (i.e., balloon angioplasty or transplantation) and for a longer duration for the treatment of chronic disorders. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

The following provides the preparation of representative compounds of this invention.

EXAMPLE 1

N-(Hepta-O-acetyl-1-deoxy-β-D-maltosyl )-4-chloro-3-nitro-benzamide

Step 1

Hepta-O-acetyl-1-β-maltosylamine

Hepta-O-acetyl-1-β-maltosylamine was obtained by the platinum oxide reduction of the azide prepared by the method of A. Bertho, *Justus Liebigs Ann. Chem.*, 562, 229 (1949).

Step 2

N-(Hepta-O-acetyl-1-deoxy-β-D-maltosyl)-4-chloro-3-nitro-benzamide

To a stirred solution of 4-chloro-3-nitrobenzoic acid (3.806 g, 0.0189 mol) in benzene-ethanol (1:1, v/v, 140 ml) was added in one portion 2-ethoxy-N-carbonyl-1,2-dihydroquinoline (5.057 g, 0.0205 mol). After 0.5 h, Hepta-O-acetyl-1-β-maltosylamine (10.0 g 0.0157 mol) was added and the mixture was stirred overnight at room temperature. The solvents were evaporated and the residue dissolved in methylene chloride. The organic layer was washed successively with 1 N hydrochloric acid, water, 1% sodium hydrogencarbonate, and water, dried (MgSO4) and concentrated. Purification by flash chromatography (40%–60% EtOAc/petroleum ether gradient) afforded 10.785 g (84%) of the title compound as a white solid, mp 185° C.; $^1$H NMR (CDCl$_3$) δ2.011 (s, 3H), 2.029 (s, 3H), 2.032 (s, 3H), 2.062 (s, 3H), 2.081 (s, 3H), 2.101 (s, 3H), 2.133 (s, 3H), 3.86–3.96 (m, 2H), 4.02–4.07 (m, 2H), 4.21–4.28 (m, 2H), 4.47 (dd, J=12.3, 2.2 Hz, 1H), 4.83–4.89 (m, 2H), 5.07 (apparent t, J=10.1 Hz, 1H), 5.34–5.49 (m, 4H), 7.04 (d, J=9 Hz, 1H), 7.65 (d, J=8.3 Hz, 1H), 7.85 (dd, J=8.6, 2.2, Hz, 1H), 8.27 (d, J=2.2 Hz, 1H). IR (KBr) 2950, 1750, 1250 and 1050 cm$^{-1}$, mass spectrum (FAB), m/e 819 (M+H), 841 (M+Na). Anal. Calcd. for $C_{33}H_{39}ClN_2O_{20}$: C, 48.39; H, 4.80; N, 3.42 Found: C, 48.33; H, 4.83; N, 3.30.

EXAMPLE 2

3-Amino-4-chloro-N-[2,3,6-tri-O-acetyl-4-O-(2,3,4,6-tetra-O-acetyl-α-D-glucopyranosyl)-β-D-glucopyranosyl}-benzamide A solution of N-(Hepta-O-acetyl-1-deoxy-β-D-maltosyl)-4-chloro-3-nitro-benzamide (1.355 g, 1.65 mmol) and tin (II) chloride dihydrate (1.87 g, 8.27 mmol) in EtOAc (40 ml) was refluxed for 2 h. The reaction was cooled to room temperature, carefully quenched with sat. aq. NaHCO$_3$ (until basic), diluted with EtOAc (250 ml), stirred overnight and filtered. The biphasic filtrate was separated and the aqueous phase extracted with EtOAc. The combined organic extracts were dried (MgSO$_4$) and concentrated. Purification by flash chromatography (30% EtOAc/methylene chloride) gave 0.953 g (76%) of 3-Amino-4-chloro-N-[2,3,6-tri-O-acetyl-4-O-(2,3,4,6-tetra-O-acetyl-α-D-glucopyranosyl )-β-D-glucopyranosyl}-3-nitro-benzamide as a white solid, mp 115–119° C.; $^1$H NMR (CDCl$_3$) δ2.00 (s, 3H), 2.01 (s, 3H), 2.03 (s, 3H), 2.05 (s, 3H), 2.08 (s, 3H), 2.10 (s. 3H), 2.13 (s, 3H), 3.85–3.89 (m, 1H), 3.92–3.96 (m, 1H), 3.99–4.07 (m, 2H), 4.25 (dt, J=12.5, 4.2 Hz, 2H), 4.45 (dd, J=12.3, 2.6 Hz, 1H), 4.84–4.89 (m, 2H), 5.07 (t, J=10.1 Hz, 1H), 5.39–5.47 (m, 4H), 6.83 (d, J=9.2 Hz, 1H), 6.95 (dd, J=8.35, 2 Hz, 1H). 7.22 (d, J=2 Hz, 1H), 7.29 (d, J=8.13 Hz, 1H). IR (KBr) 3500, 2950, 1750, 1240 and 1050 cm$^{-1}$, mass spectrum (FAB), m/e 789/791 (M+EH), 811/813 (M+Na). Anal. Calcd. for $C_{33}H_{41}ClN_2O_{18}$·0.5 H$_2$O: C, 49.66; H, 5.30; N, 3.51. Found: C, 49.62; H, 5.33; N, 3.30.

EXAMPLE 3

3-(Acetylamino)-4-chloro-N-[2,3,6-tri-O-acetyl-4-O-(2,3,4,6-tetra-O-acetyl-α-D-glucopyranosyl)-β-D-glucopyranosyl}-benzamide To a stirred solution of 3-Amino-4-chloro-N-[2,3,6-tri-O-acetyl-4-O-(2,3,4,6-tetra-O-acetyl-α-D-glucopyranosyl)-β-D-glucopyranosyl-benzamide (0.883 g, 1.17 mmol) and triethylamine (0.326 ml, 2.34 mmol) in THF (8 ml) at 0° C. was added dropwise acetyl chloride (0.1 ml, 1.4 mmol) and warmed to ambient temperature. After 4 h, the reaction was diluted with methylene chloride (20 ml), quenched with sat. aq. NaHCO$_3$ (10 ml), diluted with brine (100 ml) and extracted with methylene chloride. The combined organic extracts were dried (MgSO$_4$) and concentrated. Purification by flash chromatography (30–50% EtOAc/methylene chloride gradient) gave 0.836 g (86%) of the title compound as a white solid, mp 122–124° C.; $^1$H NMR (CDCl$_3$) δ2.00 (s, 3H), 2.01 (s, 3H), 2.03 (s, 3H), 2.05 (s, 3H), 2.08 (s, 3H), 2.10 (s. 3H), 2.13 (s, 3H), 3.85–3.89 (m, 1H), 3.92–3.96 (m, 1H), 3.99–4.06 (m, 2H), 4.25 (dt, J=12.0, 3.7 Hz, 2H), 4.45 (dd, J=12.5, 2.2 Hz, 1H), 4.86–4.93 (m, 2H), 5.07 (apparent t, J=10.1 Hz, 1H), 5.35–5.46 (m, 4H), 7.06 (d, J=8.8 Hz, 1H), 7.45 (d, J=8.3 Hz, 1H), 7.52 (dd, J=8.3, 2.2 Hz, 1H), 7.64 (s, 1H), 8.71 (s, 1H). IR (KBr) 3400, 2950, 1750, 1245 and 1050 cm$^{-1}$, mass spectrum (FAB), m/e 831/833 (M+H), 853/855 (M+Na). Anal. Calcd. for $C_{35}H_{43}ClN_2O_{19}$·0.5 H$_2$O: C, 50.04; H, 5.28; N, 3.33. Found: C, 49.87; H, 5.25; N, 3.13.

EXAMPLE 4

(R)-3-(Acetylamino)-4-chloro-N-[4,6-O-(phenylmethylene)-α-D-glucopyranosyl]-β-D-glucopyranosyl]-benzamide Step 1

3-(Acetylamino)-4-chloro-N-[4-O-α-D-glucopyranosyl)-β-D-glucopyranosyl}-benzamide To a solution of 3-(Acetylamino)-4-chloro-N-[2,3,6-tri-O-acetyl-4-O-(2,3,4,1-tetra-O-acetyl-α-D-glucopyranosyl)-β-D-glucopyranosyl}-benzamide (738 mg, 0.90 mmol) in methanol (5 ml) was added 0.075 ml of a 0.34 M solution of sodium methoxide. The reaction was stirred overnight and quenched with Dowex H+ resin. After 0.5 hr the solution filtered and concentrated in vacuo to give 461 mg (97%) of the title compound as a white solid, mp decomposed at 165; $^1$H NMR (DMSO-d$_6$) δ2.10 (s, 3H), 3.06 (apparent t, J=9.0

Hz, 1H), 3.22–3.70 (m, 12H), 4.96 (apparent t, J=8.8 Hz, 1H), 5.04 (d, J=4.0 Hz, 1H), 7.60 (d, J=8.3 Hz 1H), 7.72 (dd, J=8.3 Hz, 2.2 Hz, 1H), 8.17 (d, J=2.0 Hz, 1H) 8.98 (d, J=8.8 Hz, 1H), 9.67 (s, 1H). IR (KBr) 3375, 2900, 1660, 1550 and 1050 cm$^{-1}$, mass spectrum (FAB), m/e 537/539 (M+H), 559/561 (M+Na). Anal. Calcd. for $C_{21}H_{29}ClN_2O_{12}.H_2O$ C, 45.05; H, 5.63; N, 5.05. Found: C, 45.35; H, 5.75; N, 5.21.

Step 2

(R)-3-(Acetylamino)-4-chloro-N-[4-O-[4,6-O-(phenylmethylene)-α-D-glucopyranosyl]-β-D-glucopyranosyl]-benzamide A solution containing 3-(Acetylamino)-4-chloro-N-[4-O-α-D-gluco-pyranosyl)-β-D-glucopyranosyl}-benzamide (0.40 g, 0.7468 mmol), benzaldehyde dimethyl acetal (0.17 ml, 1.12 mmol) and camphorsulfonic acid (10 mg, 0.043 mmol) was heated at 70° C. After 4 h, the reaction was cooled to ambient temperature and quenched with 0.5 ml of a 1N NaOH solution. The solution was concentrated and purified by flash chromatography (2, 5–10% MeOH/ methylene chloride gradient) gave 0.327 g (70%) of the title compound as a white solid, mp 175° C.; $^1$H NMR (DMSO-d$_6$) δ2.1 (s, 3H), 3.35–3.40 (m, 5H), 3.49–3.62 (m, 3H), 3.64–3.77 (m, 3H), 4.12 (dd, J=9.2, 4.2 Hz, 1H), 4.66 (bs, 1H), 4.99 (apparent t, J=8.8 Hz, 1H), 5.07 (d, J=5.9 Hz, 1H), 5.16 (d, J=4.0 Hz, 1H), 5.32 (d, J=4.6 Hz, 1H), 5.57 (s, 1H), 5.59 (d, J=2.2 Hz, 1H), 5.70 (d, J=6.2 Hz, 1H), 7.35–7.40 (m, 3H), 7.43–7.46 (m, 2H), 7.60 (d, J=8.3 Hz, 1H), 7.73 (dd, J=8.3, 2.0 Hz, 1H), 8.17 (d, J=1.5 Hz, 1H), 8.99 (d, J=8.8 Hz, 1H), 9.68 (s, 1H). IR (KBr) 3400, 2900, 1650 and 1075 cm$^{-1}$, mass spectrum (+FAB), m/e 625/627 (M+H), 647/649 (M+Na). Anal. Calcd. for $C_{28}H_{33}ClN_2O_{12}.0.5 H_2O$: C, 53.04; H, 5.41; N, 4.42. Found: C, 52.86; H, 5.45; N, 4.5.

EXAMPLE 5

(R)-4-chloro-3-nitro-N-[4-O-[4,6-O-(phenylmethylene)-α-D-glucopyranosyl]-β-D-glucopyranosyl]-benzamide Step 1

4-chloro-N-(4-O-α-D-glucopyranosyl-β-D-glucopyranosyl)-3-nitro-benzamide Hydrate The title compound was prepared according to the procedure of Example 4 as a white solid, mp decomposed at 150; $^1$H NMR (CD$_3$OD-d$_4$) δ3.44–3.57 (m, 3H), 3.59–3.74 (m, 6H), 3.83–3.85 (m, 3H), 5.13 (d, J=9.2 Hz, 1H), 5.18 (d, J=3.7 Hz, 1H), 7.79 (d, J=8.3 Hz 1H), 8.12 (dd, J=8.3 Hz, 2.2 Hz, 1H), 8.47 (d, J=2.2 Hz, 1H). IR (KBr) 3400, 2900, 1670, 1550 and 1050 cm$^{-1}$, mass spectrum (ESI), m/e 523 (M–H). Anal. Calcd. for $C_{19}H_{25}ClN_2O_{13}.H_2O$ C, 42.04; H. 4.97; N, 5.16. Found: C, 42.30; H, 5.12; N, 4.96.

Step 2

(R)-4-chloro-3-nitro-N-[4-O-[4,6-O-(phenylmethylene)-α-D-glucopyranosyl]-β-D-glucopyranosyl]-benzamide The title compound was prepared according to the procedure of Example 4 as a white solid, mp 235° C.; $^1$H NMR (DMSO-d$_6$) δ3.35–3.42 (m, 5H), 3.50–3.63 (m, 3H), 3.65–3.75 (m, 3H), 4.12 (dd, J=9.2, 4.4 Hz, 1H), 4.64 (apparent t, J=5.5 Hz, 1H), 4.99 (apparent t, J=9.0 Hz, 1H), 5.16–5.19 (m, 5.9 Hz, 2H), 5.32 (d, J=5.3 Hz, 1H), 5.57 (s, 1H), 5.62 (d, J=3.3 Hz, 1H), 5.69 (d, J=6.6 Hz, 1H), 7.35–7.38 (m, 3H), 7.43–7.46 (m, 2H), 7.93 (d, J=8.6 Hz, 1H), 8.2 (dd, J=8.6, 2.0 Hz, 1H), 8.58 (d, J=2.0 Hz, 1H), 9.29 (d, J=8.8 Hz, 1H). IR (KBr) 3400, 2900, 1650 1550, and 1075 cm$^{-1}$, mass spectrum (ESI), m/z 613.1/615.2 (M+H), 630.2/632.2 (M+NH$_4$). Anal. Calcd. for $C_{26}H_{29}ClN_2O_{13}0.05H_2O$: C, 50.21; H, 4.86; N, 4.50. Found: C, 50.48; H, 4.67; N, 4.38.

EXAMPLE 6

(R)-3-(Acetylamino)-N-[6-O-benzoyl-4-O-[4,6-O-(phenylmethylene)-α-D-glucopyranosyl]-β-D-glucopyranosyl]-4-chloro-benzamide A solution of (R)-3-(Acetylamino)-4-chloro-N-[4-O-[4,6-O-(phenyl-methylene)-α-D-glucopyranosyl]-β-D-glucopyranosyl]-benzamide (0.20 g, 0.32 mmol) in dry tetrahydrofuran (1.5 ml) and anhydrous 2,4,6 collidine (1.5 ml) was cooled to −40° C. for 0.5 h. Benzoyl chloride (0.047 ml, 0.384 mmol) was added slowly and the reaction allowed to warm to ambient temperature overnight. The reaction was diluted with ethyl acetate (30 ml), and washed consecutively with 1 N HCl (15 ml), saturated aqueous sodium bicarbonate (15 ml), and brine (15 ml). The organic layer was dried (MgSO$_4$) and filtered. Evaporation and flash chromatography (2, 5–10% MeOH/methylene chloride gradient) gave 0.327 g (70%) of the title compound as a white solid, mp 225° C.; $^1$H NMR (DMSO-d$_6$) δ2.09 (s, 3H), 3.29–3.36 (m, 1H), 3.39–3.41 (m, 1H), 3.49–3.66 (m, 5H), 3.71–3.76 (m, 1H), 3.84 (bs, 1H), 4.00 (dd, J=9.7, 4.8 Hz, 1H), 4.34 (dd, J=12.5, 4.0 Hz, 1H), 4.51 (d, J=11.2 Hz, 1H), 5.08 (apparent t, J=8.8 Hz, 1H), 5.15 (d, J=3.7 Hz, 1H), 5.21 (bs, 1H), 5.36 (bs, 1H), 5.51 (s, 1H) 5.67 (s, 1H), 5.86 (bs, 1H), 7.35–7.37 (m, 3H), 7.40–7.43 (m, 2H), 7.52 (t, J=7.9 Hz, 1H), 7.59 (d, J=8.3 Hz, 1H), 7.63–7.67 (m, 1H), 7.73 (dd, J=8.6, 2.0 Hz, 1H), 7.96 (dd, J=8.6, 1.1 Hz, 1H), 8.17 (d, J=1.8 Hz, 1H), 9.05 (d, J=8.8 Hz, 1H), 9.66 (s, 1H). IR (KBr) 3400, 2900, 1660, 1275 and 1075 cm$^{-1}$, mass spectrum (+FAB), m/z 729/731 (M+H), 751/753 (M+Na). Anal. Calcd. for $C_{33}H_{37}ClN_2O_{13}.1.0H_2O$: C, 56.27; H, 5.26; N, 3.75. Found: C, 56.34; H, 5.18; N, 3.68.

EXAMPLE 7

(R)-4-chloro-N-[(6-O-benzoyl-4',6'-O-benzylidene)-β-D-maltosyl]-3-nitro-benzamide The title compound was prepared according to the procedure of Example 6 as a white solid, mp 174° C.; $^1$H NMR (DMSO-d$_6$) δ3.34–3.66 (m, 7H), 3.69–3.73 (m, 1H), 3.87 (bd, J=4.0 Hz, 1H), 4.01 (dd, J=10.1, 4.6 Hz, 1H), 4.34 (dd, J=12.0, 4.0 Hz, 1H), 4.52 (d, J=11.4 Hz, 1H), 5.09 (apparent t, J=9.0 Hz, 1H), 5.18 (d, J=3.7 Hz, 1H), 5.30 (d, J=5.3 Hz, 1H), 5.35 (d, J=5.1 Hz, 1H), 5.51 (s, 1H), 5.69 (s, 1H), 5.83 (d, J=6.2 Hz, 1H), 7.34–7.37 (m, 3H), 7.40–7.43 (m, 2H), 7.52 (apparent t, J=7.9 Hz, 1H), 7.63–7.67 (m, 1H), 7.90–7.96 (m, 3H), 8.20 (dd, J=8.6, 2.0 Hz, 1H), 8.58 (d, J=2.0 Hz, 1H) 9.34 (d, J=8.8 Hz, 1H). IR (KBr) 3400, 2900, 1725, 1550, and 1075 cm$^{-1}$, mass spectrum (+FAB), m/z 717/719 (M+H), 739/741 (M+Na). Anal. Calcd. for $C_{33}H_{33}ClN_2O_{14}.1.0H_2O$: C, 53.92; H, 4.80; N, 3.81. Found: C, 54.09; H, 4.77; N, 3.64.

EXAMPLE 8

4-Chloro-N-[(2,2',3,3'-tetra-O-acetyl-6-benzoyl-4',6'-O benzylidene)-β-D-maltosyl]-3-nitro-benzamide At 0° C., to a stirred solution containing (R)-4-chloro-N-[(6-O-benzoyl-4',6'-O-benzylidene)-β-D-maltosyl]-3-nitro-benzamide (2.33 g, 3.2493 mmol), triethylamine (3.62 ml, 25.98 mmol) and catalytic 4-dimethylaminopyridine in anhydrous methylene chloride (60 ml) was added acetic anhydride (2.15 ml, 22.75 mmol). After 6 h, the reaction was diluted with methylene chloride (100 ml), washed successively with sat. aq. NaHCO$_3$ (2x), and brine (2x), dried (MgSO$_4$) and concentrated. Purification by flash chromatography (40%–50% EtOAc/petroleum ether gradient) gave 2.865 g (99%) of the title compound as a white solid, mp 230° C.;

$^1$H NMR (CDCl$_3$) δ2.04 (s, 3H), 2.05 (s, 3H), 2.09 (s, 3H), 2.11 (s, 3H), 3.54–3.63 (m, 2H), 3.82–3.85 (m, 1H), 3.97–4.04 (m, 2H), 4.23 (apparent t, J=1H), 4.51 (dd, J=12.3, 3.5 Hz, 1H), 4.85–4.93 (m, 3H), 5.41–5.56 (m, 5H), 6.94 (d, J=9.0 Hz, 1H), 7.32–7.34 (m, 3H), 7.36–7.40 (m, 2H), 7.45 (t, J=8.0 Hz, 1H), 7.55–7.60 (m, 2H), 7.62 (d, J=8.6 Hz, 1H), 7.83 (dd, J=8.4, 2.2 Hz, 1H), 8.05 (dd, J=7.7, 0.7 Hz, 1H), 8.23 (d, J=2.0 Hz, 1H). IR (KBr) 3400, 2930, 1750, 1550, 1245 and 1075 cm$^{-1}$, mass spectrum (+FAB), m/z 885/887 (M+H), 907/909 (M+Na). Anal. Calcd. for $C_{41}H_{41}ClN_2O_{18}$: C, 55.63; H, 4.67; N, 3.16. Found: C, 55.61; H, 4.77; N, 2.92.

EXAMPLE 9

(R)-N-[2-O-Acetyl-4-O-[2-O-acetyl-4,6-O-(phenylmethylene)-α-D-glucopyranosyl]-6-O-benzoyl-β-D-glucopyranosyl]-3-(acetylamino)-4-chlorobenzamide The title compound was prepared according to the procedure of Example 8 as a white solid; $^1$H NMR (DMSO-d$_6$) δ1.94 (s, 3H), 2.07 (s, 3H), 2.08 (s, 3H), 3.48 (apparent t, J=9.4 Hz, 1H), 3.54 (apparent t, J=10.1 Hz, 1H), 3.64–3.67 (m, 1H), 3.77–3.87 (m, 4H), 3.95–3.99 (m, 1H), 4.36 (dd, J=12.3, 3.3 Hz, 1H), 4.59–4.59 (m, 2H), 4.85 (apparent t, J=9.2 Hz, 1H), 5.33–5.39 (m, 2H), 5.5–5.56 (m, 3H), 7.33–7.40 (m, 5H), 7.52–7.59 (m, 4H), 7.65–7.69 (m, 1H), 7.98–8.00 (m, 2H), 8.09 (s, 1H), 9.14 (d, J=9.2 Hz, 1H), 9.64 (s, 1H). IR (KBr) 3400, 2900, 1750, 1660, 1250 and 1075 cm$^{-1}$, mass spectrum (+FAB), m/z 813/815 (M+H), 835/837 (M+Na). Anal. Calcd. for $C_{39}H_{41}ClN_2O_{15}$.2.5H$_2$O: C, 54.58; H, 5.40; N, 3.26. Found: C, 54.81; H, 5.23; N, 3.28.

EXAMPLE 10

N-(Hepta-O-acetyl-β-D-maltosyl)-4-chloro-benzamide

To a stirred mixture of Hepta-O-acetyl-1-β-maltosylamine, (0.90 g, 1.42 mmol) and triethyl amine (0.538 g, 3.54 mmol) in dichloromethane (8 ml), and tetrahydrofuran (4 ml) was added in one portion 4-chlorobenzoyl chloride (0.322 g, 1.84 mmol). After 12 h, the reaction was diluted with dichloromethane (50 ml) and washed successively with water (20 ml), 10% sodium hydroxide (20 ml) and 0.1 N hydrogen chloride (20 ml), dried (MgSO$_4$) and concentrated. Purification by flash chromatography (20%–30% EtOAc/dichloromethane gradient) gave 0.70 g (74%) of the title compound as a white solid, mp 113–115° C.; $^1$H NMR (CDCl$_3$) δ2.01 (s, 6H), 2.03 (s, 3H), 2.06 (s, 3H), 2.08 (s, 3H), 2.10 (s, 3H), 2.13 (s, 3H), 3.86–4.13 (m, 4H), 4.21–4.29 (m, 2H), 4.45 (dd, J=12.1, 2.42, Hz, 2H), 4.84–4.89 (m, 2H), 5.07 (aparant t, J=9.9, 1H), 5.35–5.49 (m, 4H), 6.86 (d, J=9.2, 1H), 7.42 (d, J=8.6, 2H), 7.68 (d, J=8.4, 2H). IR (KBr) 3400, 2930, 1750, 1550, 1245 and 1075 cm$^{-1}$, mass spectrum (+ESI), m/z 774 (M+H), 791 (M+NH$_4$). Anal. Calcd. for $C_{33}H_{40}ClNO_{18}$: C, 51.20; H, 5.21; N, 1.81. Found: C, 51.04; H, 5.24; N, 1.81.

EXAMPLE 11

N-(4',6'-O-Benzylidene-β-D-maltosyl)-4-chloro-benzamide

The title compound was prepared according to the procedure of Example 4 is a white solid, mp decomposed at 225–230° C.; $^1$H NMR (DMSO-d$_6$) δ3.34–3.75 (m, 11H), 4.12 (dd, J=9.4, 4.4, Hz, 1H), 4.63 (apparent t, J=5.5 Hz, 1H), 4.98 (apparent t, J=9.0 Hz, 1H), 5.09 (d, J=5.7 Hz, 1H), 5.16 (d, J=4.0 Hz, 1H), 5.31 (d, J=5.1 Hz, 1H), 5.57 (s, 1H), 5.59 (d, J=3.1 Hz, 1H), 5.69 (d, J=6.6 Hz, 1H), 7.36–7.38 (m, 3H) 7.43–7.46 (m, 2H), 7.55 (d, J=8.6, Hz, 1H), 7.93 (d, J=8.6 Hz, 1H), 8.98 (d, J=8.8 Hz, 1H). IR (KBr) 3400, 2900, 2200, 1650, 1550 and 1050 cm$^{-1}$, mass spectrum (+ESI), m/z 568 (M+H). Anal. Calcd. for $C_{26}H_{30}ClNO_{11}$.0.5H$_2$O: C, 54.12; H, 5.42; N, 2.43. Found: C, 54.16; H, 5.24; N, 2.47.

EXAMPLE 12

N-(6-O-benzoyl-4',6'-O-benzylidene-β-D-maltosyl)-4-chloro-benzamide

The title compound was prepared according to the procedure of Example 6 as a white solid, mp 250° C.; $^1$H NMR (DMSO-d$_6$) δ3.34–3.76 (m, 8H), 3.82–3.85 (m, 1H), 3.99–4.03 (m, 1H), 4.34 (dd, J=12.3, 4.0 Hz, 1H), 4.51 (d, J=12.3 Hz, 1H), 5.08 (apparent t, J=9.0 Hz, 1H), 5.17 (d, J=3.7 Hz, 1H), 5.22 (d, J=5.7 Hz, 1H), 5.36 (d, J=5.3 Hz, 1H), 5.51 (s, 1H), 5.67 (d, J=2.4 Hz, 1H), 5.85 (d, J=6.2 Hz, 1H), 7.34–7.43 (m, 5H), 7.50–7.56 (m, 4H), 7.63–7.67 (m, 1H), 7.91–7.96 (m, 4H), 9.05 (d, J=8.8 Hz, 1H). IR (KBr) 3400, 2900, 1725, 1600, 1550, and 1075 cm$^{-1}$, mass spectrum (+FAB), m/z 672 (M+H), 694 (M+Na). Anal. Calcd. for $C_{33}H_{34}ClNO_{12}$: C, 58.98; H, 5. 10; N, 2.08. Found: C, 58.54; H, 4.92; N, 2.00.

EXAMPLE 13 & 14

N-[(2,2',3,3'4',6,6'-hepta-O-acetyl-β-D-maltosyl]-3-chloro-4-nitrilobutoxy-benzoic acid amide (13)

N-[(2,2',3,3'4',6,6'-hepta-O-acetyl-α-D-maltosyl]-3-chloro-4-nitrilobutoxy-benzoic acid amide (14)

Step 1

3-Chloro-4-(4-nitrilo-butoxy)-benzoic acid methyl ester

A mixture of methyl-3-chloro-4-hydroxy benzoate (5.0 g, 26.8 mmol), 4-bromo butyronitrile (4.0 ml, 40.19 mmol), potassium carbonate (7.4 g, 53.6 mmol), and methyl sulfoxide (40 ml) in 2-butanone (100 ml) was refluxed for 24 h. The reaction mixture was cooled and filtered. The mixture was concentrated in vacuo, diluted with ethyl ether, and washed twice with water and once with saturated sodium chloride solution. The organic layer was dried (MgSO$_4$), filtered and concentrated to give 6.75 g (99%) of a light brown solid. An analytical sample was obtained lay silica gel chromatography (10%–20% EtOAc/petroleum ether gradient) mp 90° C.; $^1$H NMR (CDCl$_3$) δ2.20–2.26 (m, 2H), 2.68 (t, J=7.0 Hz, 2H), 3.90 (s, 3H), 4.21 (t, J=5.5 Hz, 2H), 6.93 (d, J=8.6 Hz, 1H), 7.93 (dd, J=8.6, 2.0 Hz, 1H), 8.06 (d, J=2.0 Hz, 1H). IR (KBr) 3400, 2280, 1700, 1600, 1500, 1245 and 1050 cm$^{-1}$, mass spectrum (EI), m/z 253/255. Anal. Calcd. for $C_{12}H_{12}ClNO_3$: C, 56.82; H, 4.77; N 5.52. Found: C, 56.69; H, 4.69; N, 5.47.

Step 2

3-Chloro-4-(4-nitrilo-butoxy)-benzoic acid

A solution of 3-Chloro-4-(4-nitrilo-butoxy)-benzoic acid methyl ester (6.24 g, 24.6 mmol in THF (100 ml) and methanol (100 ml) was treated with 5 N sodium hydroxide solution (35 ml) with stirring at room temperature for 1 h. The reaction mixture was concentrated in vacuo, diluted with water, and acidified to pH 1 with 5 N hydrochloric acid. The resulting suspension was extracted with ethyl acetate. The organic layer was dried (MgSO$_4$), filtered, and concentrated in vacuo. The resulting off white solid was triturated with hot petroleum ether, cooled and filtered to give 5.58 g (95%) of the title compound as a white solid mp 150° C.; $^1$H NMR (CDCl$_3$) δ2.22–2.28 (m, 2H), 2.69 (t, J=7.0 Hz, 2H), 3.90 (s, 3H), 4.23 (t, J=5.5 Hz, 2H), 6.97 (d, J=8.6 Hz, 1H), 8.01 (dd, J=8.6, 2.2 Hz, 1H), 8.14 (d, J=2.0 Hz, 1H). IR (KBr) 3400, 2200, 1700, 1600, 1450, 1275 and 1050 cm$^{-1}$, mass spectrum (EI), m/z 239/241. Anal. Calcd. for $C_{11}H_{10}ClNO_3$: C, 55.13; H, 4.21; N, 5.85. Found: C, 54.84; H, 4.01; N, 5.69.

Step 3

N-[(2,2',3,3'4',6,6'-hepta-O-acetyl-β-D-maltosyl]-3-chloro-4-nitrilobutoxy-benzoic acid amide The title compounds were prepared according to the following procedure. To a mixture of Hepta-O-acetyl-1-β-maltosylamine (1.255 g, 1.97 mmol) and 3-Chloro-4-(4-nitrilo-butoxy)-benzoic acid (0.591 g, 2.47 mmol) was added triethyl amine (0.40 g, 3.95 mmol), HOBT (0.480 g, 3.55 mmol) and DEC (0.567 g, 2.96 mmol). After stirring at ambient temperature overnight the reaction was concentrated and partitioned between ethyl acetate (80 ml) and 1N sodium hydroxide (50 ml). The aqueous layer was seperated and extracted with ethyl acetate (3×30 ml). The organic layers were washed with 1N hydrogen chloride (50 ml) then water (50 ml) and dried ($MgSO_4$) and concentrated. Purification by flash chromatography (20%–50% EtOAc/petroleum ether gradient) afforded 47% β anomer and 7% α anomer as white solids, β anomer mp 102–103° C.; $^1$H NMR ($CDCl_3$) δ2.011 (s, 3H), 2.01 (s, 3H), 2.03 (s, 3H), 2.05 (s, 3H), 2.08 (s, 3H), 2.10 (s, 3H), 2.13 (s, 3H), 2.19–2.26 (m, 2H), 2.67 (t, J=7.0 Hz, 2H), 3.85–4.06 (m, 4H), 4.17–4.25 (m, 3H), 4.45 (dd, J=12.7, 2.6 Hz, 1H), 4.84–4.89 (m, 2H), 5.07 (apparent t, J=10.1 Hz, 1H), 5.35–5.48 (m, 4H), 6.79 (d, J=9.2 Hz, 1H), 6.94 (d, J=8.6 Hz, 1H), 7.59 (dd, J=8.6, 2.4, Hz, 1H), 7.82 (d, J=2.2 Hz, 1H). IR (KBr) 3400, 2950, 2280, 1750, 1250 and 1050 $cm^{-1}$, mass spectrum (+ESI), m/z 857.4/859.4 (M+H), 874.4/876.3 (M+$NH_4$), 879.4/881.31 (M+Na). Anal. Calcd. for $C_{37}H_{45}ClN_2O_{19}$·1.0 $H_2O$: C, 50.78; H, 5.41; N, 3.20. Found: C, 50.93; H, 5.17; N, 3.35.

N-[2,2'3,3'4',6,6'-hepta-O-acetyl-α-D-maltosyl]-3-chloro-4-nitrilobutoxy-benzoic acid amide α anomer mp 105–106° C.; $^1$H NMR ($CDCl_3$) δ1.98 (s, 3H), 2.00 (s, 3H), 2.03 (s, 3H), 2.10 (s, 6H), 2.14 (s, 3H), 2.20–2.27 (m, 2H), 2.67 (t, J=7.0 Hz, 2H), 3.94–3.98 (m, 2H), 4.03–4.08 (m, 2H), 4.21–4.40 (m, 4H), 4.42 (d, J=2.0 Hz, 1H), 4.87 (dd, J=10.5, 4.0, Hz, 1H), 5.07 (apparent t, J=10.1 Hz, 1H), 5.18 (dd, J=9.7, 5.3, Hz, 1H), 5.33–5.44 (m, 3H), 5.95 (apparent bt, J=6.2 Hz, 1H), 6.34 (d, J=8.0 Hz, 1H), 6.97 (d, J=8.8 Hz, 1H), 7.84 (dd, J=8.8, 1.8, Hz, 1H), 7.97 (d, J=1.1 Hz, 1H). IR (KBr) 3400, 2950, 2280, 1750, 1250 and 1050 $cm^{-1}$, mass spectrum (+ESI), m/z 857.4/859.4 (M+H), 874.4/876.4 (M+$NH_4$), 879.4/881.4 (M+Na).

EXAMPLE 15

N-(4',6'-O-Benzylidene-β-D-maltosyl)-3-chloro-4-(4-nitrilo-butoxy)-benzamide

Step 1

3-chloro-4-(3-cyanopropoxy)-N-(4-O-α-D-glucopyranosyl-β-D-glucopyranosyl)-benzamide Hydrate The title compound was prepared according to the procedure of Example 4, Step 1 as a white solid, mp 203° C.; $^1$H NMR ($CD_3OD$-$d_4$) 2.15–2.22 (m, 2H), 2.70 (t, J=7.2 Hz, 2H), 3.26 (t, J=9.4 Hz, 2H), 3.43–3.53 (m, 3H), 3.57–3.73 (m, 4H), 3.78–3.84 (m, 3H), 4.23 (apparent t, J=5.7 Hz, 1H), 5.08–5.13 (m, 1H), 5.18 (d, J=3.7 Hz, 1H), 7.17 (d, J=8.8 Hz, 1H), 7.86 (dd, J=8.6, 2.0, Hz, 1H), 7.98 (d, J=2.2 Hz, 1H), 8.91 (d, J=9.0 Hz, 1H). IR (KBr) 3375, 2900, 2200, 1600, 1550 and 1050 $cm^{-1}$, mass spectrum (+FAB), m/z 563/565 (M+H), 585/587 (M+Na). Anal. Calcd. for $C_{23}H_{31}ClN_2O_{12}$·0.10$H_2O$: C, 47.55; H, 5.73; N, 4.82. Found: C, 47.26; H, 5.84; N, 4.75.

Step 2

N-(4',6'-O-Benzylidene-β-D-maltosyl)-3-chloro-4-(4-nitrilo-butoxy)-benzamide

The title compound was prepared according to the procedure of Example 4, Step 2 as a white solid, mp decomposed at 190° C.; $^1$H NMR (DMSO-$d_6$) 2.05–2.12 (m, 2H), 2.67 (t, J=7.5 Hz, 2H), 3.34–3.42 (m, 4H), 3.48–3.62 (m, 4H), 3.64–3.78 (m, 3H), 4.14 (dd, J=9.4, 4.6, Hz, 1H), 4.19 (apparent t, J=5.9 Hz, 1H), 4.62 (apparent t, J=5.5 Hz, 1H), 4.97 (apparent t, J=9.0 Hz, 1H), 5.09 (d, J=5.7 Hz, 1H), 5.16 (d, J=3.7 Hz, 1H), 5.32 (d, J=5.1 Hz, 1H), 5.57 (s, 1H), 5.59 (d, J=2.9 Hz, 1H), 5.70 (d, J=6.6 Hz, 1H), 7.26 (d, J=8.8 Hz, 1H), 7.34–7.40 (m, 3H) 7.42–7.46 (m, 2H), 7.90 (dd, J=8.6, 2.2, Hz, 1H), 8.04 (d, J=2.2 Hz, 1H), 8.89 (d, J=8.8 Hz, 1H). IR (KBr) 3400, 2900, 2200, 1650, 1550 and 1050 $cm^{-1}$, mass spectrum (+ESI), m/z 651 (M+H). Anal. Calcd. for $C_{30}H_{35}ClN_2O_{12}$: C, 55.34; H, 5.42; N, 4.30. Found: C, 55.00; H, 5.30; N, 4.10.

N-(6-O-Benzoyl-4',6'-O-benzylidene-β-D-maltosyl)-3-chloro-4-(4-nitrilo-butoxy)-phenyl amide The title compound was prepared according to the procedure of Example 6 as a white solid, mp ; $^1$H NMR (DMSO-$d_6$) 2.04–2.11 (m, 2H), 2.66 (t, J=7.2 Hz, 2H), 3.33–3.75 (m, 8H), 4.14 (bd, J=4.6, Hz, 1H), 4.00 (dd, J=9.9, 4.4, Hz, 1H), 4.18 (apparent t, J=6.0 Hz, 1H), ),4.34 (dd, J=12.3, 4.0, Hz, 1H), ), 4.50 (bd, J=11.2, Hz, 1H), 5.06 (apparent t, J=9.0 Hz, 1H), 5.17 (d, J=3.7 Hz, 1H), 5.22 (d, J=5.7 Hz, 1H), 5.36 (d, J=5.3 Hz, 1H), 5.51 (s, 1H), 5.67 (d, J=2.0 Hz, 1H), 5.85 (d, J=6.2 Hz, 1H), 7.25 (d, J=8.8 Hz, 1H), 7.34–7.40 (m, 3H) 7.41–7.43 (m, 2H), 7.52 (t, J=7.7 Hz, 1H), 7.89 (dd, J=8.6, 2.2, Hz, 1H), 7.94–7.96 (m, 2H), 8.04 (d, J=2.2 Hz, 1H), 8.95 (d, J=8.8 Hz, 1H). IR (KBr) 3400, 2900, 2200, 1650, 1550, 1225, and 1050 $cm^{-1}$, mass spectrum (+FAB), m/z 755 (M+H), 777 (M+Na). Anal. Calcd. for $C_{37}H_{39}ClN_2O_{13}$·0.5$H_2O$: C, 58.16; H, 5.28; N, 3.66. Found: C, 58.12; 5.32; N, 3.73.

EXAMPLE 17

N-(2,2',3,3'-tetra-O-Acetyl-6-O-benzoyl-4',6'-O-benzylidene-β-D-maltosyl)-3-chloro-4-(4-nitrilo-butoxy)-benzamide The title compound was prepared according to the procedure of Example 8 as a white solid, mp 230–232° C.; $^1$H NMR ($CDCl_3$) 2.02 (s, 3H), 2.04 (s, 3H), 2.07 (s, 3H), 2.11 (s, 3H), 2.20–2.24 (m, 2H), 2.66 (t, J=7.0 Hz, 2H), 3.52–3.62 (m, 2H), 3.81–3.87 (m, 1H), 3.95–4.04 (m, 2H), 4.17 (apparent t, J=5.5 Hz, 2H), 4.22 (apparent t, J=9.5 Hz, 1H), 4.51 (dd, J=12.5, J=3.0, Hz, 1H), 4.84–4.93 (m, 3H), 5.40 (s, 1H), 5.43–5.54 (m, 4H), 7.73 (d, J=9.2 Hz, 1H), 6.91 (d, J=8.8 Hz, 1H), 7.31–7.39 (m, 5H) 7.43–7.47 (m, 2H), 7.55–7.60 (m, 2H), 7.78 (d, J=2.2 Hz, 1H), 8.04–8.07 (m, 2H). IR (KBr) 3400, 2900, 2200, 1750, 1650, 1550, 1250 and 1050 $cm^{-1}$, mass spectrum (+FAB), m/z 923 (M+H), 945 (M+Na).

EXAMPLE 18

4-butoxy-3-chloro-N-[2,3,6-tri-O-acetyl-4-O-(2,3,4,6-tetra-O-acetyl-α-D-glucopyranosyl)-β-D-glucopyranosyl]benzamide Step 1

3-Chloro-4-(4-nitrilo-butoxy)-benzoic acid methyl ester

The title compound was prepared according to the procedure of Example 13, Step 1 affording 95% as a clear oil; $^1$H NMR ($CDCl_3$) δ1.0 (t, J=7.2 Hz, 3), 1.49–1.58 (m, 2H) 1.81–1.88 (m, 2H), 3.89 (s, 3H), 4.09 (t, J=6.6 Hz, 2H), 6.92 (d, J=8.8 Hz, 1H), 7.91 (dd, J=8.6, 2.2 Hz, 1H), 8.05 (d, J=2.2 Hz, 1H). IR (KBr) 2950, 1675, 1600, 1500, 1225 and 1050 $cm^{-1}$, mass spectrum (−ESI), m/z 227.3. Anal. Calcd. for $C_{11}H_{13}ClO_3$: C, 57.78; H, 5.73. Found: C, 57.89; H, 5.62.

Step 2
3-Chloro-4-(4-nitrilo-butoxy)-benzoic acid methyl ester

The title compound was prepared according to the procedure of Example 13, Step 2 affording 95% as a white solid, mp 144° C.; $^1$H NMR (CDCl$_3$) δ1.0 (t, J=7.5 Hz, 3), 1.50–1.60 (m, 2H) 1.83–1.90 (m, 2H), 4.12 (t, J=6.4 Hz, 2H), 6.96 (d, J=8.8 Hz, 1H), 7.98 (dd, J=8.6, 2.2 Hz, 1H), 8.12 (d, J=2.2 Hz, 1H). IR (KBr) 2950, 1700, 1600, 1500, 1225 and 1050 cm$^{-1}$, mass spectrum (+EI), m/z 242/244. Anal. Calcd. for C$_{12}$H$_{15}$ClO$_3$: C, 59.39; H, 6.23. Found: C, 59.22; H, 6.25.

Step 3
4-butoxy-3-chloro-N-[2,3,6-tri-O-acetyl-4-O-(2,3,4,6-tetra-O-acetyl-α-D-glucopyranosyl)-β-D-glucopyranosyl] benzamide The title compound was prepared according to the procedure of Example 10, Step 3 affording 92% as a white solid, mp ° C.; $^1$H NMR (CDCl$_3$) δ0.99 (t, 7.5 Hz, 3H), 1.50–1.58 (m, 2H), 1.80–1.87 (m, 2H), 2.01 (s, 6H), 2.03 (s, 3H), 2.05 (s, 3H), 2.08 (s, 3H), 2.10 (s, 3H), 2.13 (s, 3H), 3.86–3.89 (m, 1H), 3.92–3.96 (m, 1H), 3.99–4.09 (m, 4H), 4.45 (dd, J=12.3, 2.4 Hz, 1H), 4.84–4.90 (m, 2H), 5.07 (apparent t, J=9.7 Hz, 1H), 5.35–5.48 (m, 4H), 6.76 (d, J=9.2 Hz, 1H), 6.92 (d, J=4.3 Hz, 1H), 7.57 (dd, J=8.6, 2.2, Hz, 1H), 7.80 (d, J=2.4 Hz, 1H). IR (KBr) 3400, 2950, 1750, 1250 and 1050 cm$^{-1}$, mass spectrum (+ESI), m/z 846.1/848.1 (M+H), 863.1 (M+NH$_4$). Anal. Calcd. for C$_{37}$H$_{48}$ClN$_2$O$_{19}$: C, 52.52; H, 5.72; N, 1.65. Found: C, 52.31; H, 5.64; N, 1.61.

EXAMPLE 19

4-Butoxy-3-chloro-N-[(4',6'-O-benzylidene)-β-D-maltosyl]-benzamide hydrate

Step 1
4-Butoxy-3-chloro-N-(β-D-maltosyl)-benzamide Hydrate

The title compound was prepared according to the procedure of Example 4, Step 1 as a white solid, mp decomposition at 180; $^1$H NMR (CD$_3$OD-d$_4$) 0.94 (t, 7.2 Hz, 3H), 1.41–1.50 (m, 2H), 1.70–1.77 (m, 2H), 3.03–3.09 (m, 1H), 3.17 (d 4.8 Hz, 1H), 3.22–3.70 (m, 11H), 4.12 (apparent t, J=6.4 Hz, 1H), 4.46–4.51 (m, 2H), 4.90 (bd, J=4.2 Hz, 2H), 4.95 (t, J=9.0 Hz, 1H), 5.05 (bd, 3.7 Hz, 1 Hz), 5.06 (bs, 1Hz), 5.5 (bs, 1Hz), 5.6 (bs, 1 Hz), 7.23 (d, J=8.8 Hz, 1H), 7.88 (dd, J=8.6, 2.2, Hz, 1H), 8.02 (d, J=2.2 Hz, 1H), 8.86 (d, 4.4 Hz, 1 Hz). IR (KBr) 3375, 2900, 1600, 1550 and 1050 cm$^{-1}$, mass spectrum (−ESI), m/z 550.1 (M−H). Anal. Calcd. for C$_{23}$H$_{24}$ClNO$_{12}$.0.5 H$_2$O: C, 49.25; H, 6.29; N, 2.50. Found: C, 49.28; H, 6.27; N, 2.49.

Step 2
4-Butoxy-3-chloro-N-[(4',6'-O-benzylidene)-β-D-maltosyl]-benzamide Hydrate The title compound was prepared according to the procedure of Example 4, Step 2 as a white solid, mp decomposed at 215–220; $^1$H NMR (DMSO-d$_6$) 0.94 (t, 7.2 Hz, 3H), 1.41–1.51 (m, 2H), 1.70–1.77 (m, 2H), 3.28–3.42 (m, 4H) 3.48–3.65 (m, 4H), 3.67–3.78 (m, 4H), 4.12 (apparent t, J=6.2 Hz, 3H), 4.63 (apparent t, J=5.5 Hz, 1H), 4.97 (apparent t, J=8.8 Hz, 1H), 5.15 (apparent t, J=7.7 Hz, 1H), 5.34 (d, J=5.1 Hz, 1H), 5.57 (s, 1H), 5.62 (d, J=2.9 Hz, 1H), 5.73 (d, J=6.6 Hz, 1H), 7.23 (d, J=9.0 Hz, 1H), 7.34–7.40 (m, 3H), 7.43–7.46 (m, 2H), 7.88 (dd, J=8.8, 2.2, Hz, 1H), 8.03 (d, J=2.2 Hz, 1H), 8.90 (d, J=8.8 Hz, 1H). IR (KBr) 3400, 2900, 1650, 1550 and 1050 cm$^{-1}$, mass spectrum (+FAB) m/z 640/642 (M+H), 662/664 (M+Na). Anal. Calcd. for C$_{30}$H$_{38}$ClNO$_{12}$.0.5H$_2$O: C, 55.52; H, 6.06; N, 2.16. Found: C, 55.72; H, 6.01; N, 2.07.

EXAMPLE 20

4-Butoxy-3-chloro-N-[(6-O-benzoyl-4',6'-O-benzylidene)-β-D-maltosyl]-benzamide

The title compound was prepared according to the procedure of Example 6 as a white solid, mp 224; $^1$H NMR (DMSO-d$_6$) 0.92 (t, 7.5 Hz, 3H), 1.42–1.47 (m, 2H), 1.69–1.74 (m, 2H), 3.33–3.65 (m, 7H), 3.69–3.73 (m, 1H), 3.81–3.83 (m, 1H), 4.0 (dd, J=9.9, 4.8, Hz, 1H), 4.12 (apparent t, J=6.4 Hz, 2H), 4.33 (dd, J=12.3, 3.7, Hz, 1H), 4.50 (d, J=11 Hz, 1H), 5.06 (apparent t, J=9.0 Hz, 1H), 5.17 (d, J=4.0 Hz, 1H), 5.21 (d, J=5.7 Hz, 1H), 5.36 (d, J=5.1 Hz, 1H), 5.51 (s, 1H), 5.67 (d, J=2.0 Hz, 1H), 5.85 (d, J=6.2 Hz, 1H), 7.22 (d, J=8.8 Hz, 1H), 7.35–7.37 (m, 3H), 7.40–7.43 (m, 2H), 7.52 (t, J=8.0 Hz, 1H), 7.63–7.67 (m, 1H), 7.88 (dd, J=8.6, 2.2, Hz, 1H), 7.95 (d, J=8.3 Hz, 1H), 8.02 (d, J=2.2 Hz, 1H), 8.02 (d, J=2.2 Hz, 1H). 8.93 (d, J=8.8 Hz, 1H). IR (KBr) 3400, 2900, 1650, 1500, 1225 and 1050 cm$^{-1}$, mass spectrum (+FAB) m/z 744/746 (M+H), 766/768 (M+Na). Anal. Calcd. for C$_{37}$H$_{42}$ClNO$_{13}$: C, 59.72; H, 5.69; N, 1.88. Found: C, 59.61; H, 5.84; N, 1.87.

EXAMPLE 21

4-Butoxy-3-chloro-N-[(2,3,2',3'-tetra-O-acetyl-6-O-benzoyl-4',6'-O-benzylidene)-β-D-maltosyl]-benzamide The title compound was prepared according to the procedure of Example 8 as a white solid, mp 260–261; $^1$H NMR (CDCl$_3$) 0.98 (t, 7.5 Hz, 3H), 1.49–1.55 (m, 2H), 1.79–1.84 (m, 2H), 2.02 (s, 3H), 2.04 (s, 3H), 2.07 (s, 3H), 2.11 (s, 3H), 3.52–3.61 (m, 2H), 3.82–3.85 (m, 1H), 3.95–4.03 (m, 3H), 4.06 (apparent t, J=6.4 Hz, 1H), 4.22 (apparent t, J=6.4 Hz, 1H), 4.51 (dd, J=12.5, 3.1, Hz, 1H), 4.83–4.93 (m, 3H), 5.40 (s, 1H), 5.43–5.54 (m 4H), 6.70 (d, J=9.2 Hz, 1H), 6.90 (d, J=8.8 Hz, 1H), 7.31–7.34 (m, 3H), 7.36–7.40 (m, 2H), 7.43–7.47 (m, 2H), 7.55–7.59 (m, 2H), 7.76 (d, J=2.2, Hz, 1H), 8.05 (d, J=1.3 Hz, 1H), 8.07 (d, J=1.3 Hz, 1H). IR (KBr) 3400, 2900, 1750, 1500, 1250 and 1050 cm$^{-1}$, mass spectrum (+FAB) m/z 912/914 (M+H), 934/936 (M+Na). Anal. Calcd. for C$_{43}$H$_{50}$ClNO$_{17}$: C, 59.24; H, 5.52; N, 1.54. Found: C, 59.24; H, 5.59; N, 1.61.

EXAMPLE 22

4-Chloro-3-methoxy-N-[2,3,6-tri-O-acetyl-4-O-(2,3,4,6-tetra-O-acetyl-α-D-glucopyranosyl)-β-D-glucopyranosyl]benzamide The title compound was prepared according to the procedure of Example 10affording 83% as a white solid, mp 106–110° C.; $^1$H NMR (DMSO-d$_6$) δ1.86 (s, 6H), 1.95 (s, 3H), 1.98 (s, 3H), 2.00 (s, 3H), 2.01 (s, 3H), 2.04 (s, 3H), 3.87–4.02 (m, 3H), 3.90 (s, 3H), 4.11–4.17 (m, 3H), 4.35 (bd, J=9.9 Hz, 1H), 4.87 (dd, J=1.05, 3.7 Hz, 1H), 4.98 (q, J=10.1 Hz, 2H), 5.23 (apparent t, J=9.7 Hz, 1H), 5.34 (d, J=3.7 Hz, 1H), 5.44 (apparent t, J=9.2 Hz, 1H), 5.59 (apparent t, J=9.2 Hz, 1H), 7.40 (dd, J=8.4, 1.8 Hz, 1H), 7.50 (d, J=1.8 Hz, 1H), 7.54 (d, J=8.4, Hz, 1H), 9.21 (d, J=4.6 Hz, 1H). IR (KBr) 3400, 2950, 1750, 1250 and 1050 cm$^{-1}$, mass spectrum (+ESI), m/z (M+H), (M+NH$_4$). Anal. Calcd. for C$_{34}$H$_{42}$ClNO$_{19}$: C, 50.78; H, 5.26; N, 1.74. Found: C, 50.2; H, 5.06; N, 1.59.

EXAMPLE 23

N-(4',6'-O-Benzylidene-β-D-maltosyl)-4-chloro-3-methoxy-benzamide

Step 1
N-(β-D-Maltosyl)-4-chloro-3-methoxy-benzamide

The title compound was prepared according to the procedure of Example 4, Step 1 affording a white solid, mp 165–168√ C.; $^1$H NMR (CD$_3$OD-d$_4$) δ3.24–3.24 (m, 2H), 3.44–3.89 (m, 10H), 3.95 (s, 3H), 5.12–5.29 (m, 2H), 7.45

(d, J=1.3 Hz, 2H), 7.58 (s, 1H), 8.98 (d, J=9.0, Hz, 1H). IR (KBr) 3400, 2950, 1650, 1250 and 1045 cm$^{-1}$, mass spectrum (+FAB), m/z 510/512 (M+H), 532/534 (M+NH$_4$). Anal. Calcd. for C$_{20}$H$_{28}$ClNO$_{12}$·0.5H$_2$O: C, 46.29; H, 5.63; N, 2.70. Found: C, 46.43; H, 5.81; N, 2.67.

Step 2

N-(4',6'-O-Benzylidene-β-D-maltosyl)-4-chloro-3-methoxy-benzamide

The title compound was prepared according to the procedure of Example 4, Step 2 affording a white solid; $^1$H NMR (DMSO-d$_6$) δ3.34–3.43 (m, 4H), 3.49–3.75 (m, 6H), 3.93 (s, 3H), 4.08–4.14 (m, 2H), 4.65 (apparent t, J=5.3 Hz, 1H), 5.01 (apparent t, J=8.8 Hz, 1H), 5.12 (d, J=5.7 Hz, 1H), 5.16 (d, J=3.7 Hz, 1H), 5.28 (d, J=5.1 Hz, 1H), 5.57 (s, 1H), 5.61 (d, J=3.1 Hz, 1H), 5.71 (d, J=6.6 Hz, 1H), 7.35–7.40 (m, 3H), 7.43–7.46 (m, 2H), 7.49–7.55 (m, 2H), 7.61 (d, J=1.3 Hz, 1H), 8.98 (d, J=8.8, Hz, 1H). IR (KBr) 3400, 2900, 1650, 1300 and 1075 cm$^{-1}$, mass spectrum (+FAB), m/z 599 (M+H), 620/622 (M+Na). Anal. Calcd. for C$_{27}$H$_{32}$ClNO$_{12}$: C, 54.23; H, 5.39; N, 2.34. Found: C, 54.27; H, 5.50; N, 2.25.

EXAMPLE 24

N-(6-O-Benzoyl-4',6'-O-benzylidene-β-D-maltosyl)-4-chloro-3-methoxy-benzamide

The title compound was prepared according to the procedure of Example 6 affording a white solid, mp 245° C.; $^1$H NMR (DMSO-d$_6$) δ3.34–3.74 (m, 8H), 3.84–3.87 (m, 1H), 3.91 (s, 3H), 4.00 (dd, J=9.9, 4.8 Hz, 1H), 4.35 (dd, J=12.3, 4.2 Hz, 1H), 4.51 (d, J=11.0 Hz, 1H), 5.10 (apparent t, J=9.0 Hz, 1H), 5.17 (d, J=3.7 Hz, 1H), 5.26 (d, J=5.7 Hz, 1H), 5.37 (d, J=5.1 Hz, 1H), 5.51 (s, 1H), 5.69 (d, J=2.4 Hz, 1H), 5.86 (d, J=6.4 Hz, 1H), 7.35–7.37 (m, 3H), 7.38–7.43 (m, 2H), 7.49–7.54 (m, 4H), 7.61–7.67 (m, 2H), 7.95 (dd, J=8.6, 1.0 Hz, 1H), 9.04 (d, J=9.0, Hz, 1H). IR (KBr) 3400, 2900, 1650, 1250 and 1055 cm$^{-1}$, mass spectrum (+FAB), m/z 702 (M+H), 724 (M+Na). Anal. Calcd. for C$_{34}$H$_{36}$ClNO$_{13}$·0.5H$_2$O: C, 57.43; H, 5.24; N, 1.97. Found: C, 57.34; H, 5.27; N, 1.96.

EXAMPLE 25

N-(2,2',3,3',4,6,6'-hepta-O-acetyl-β-D-maltosyl]-4-butoxy-5-chloro-3-methoxy-benzamide The title compound was prepared according to the procedure of Example 10 affording 88% as a white solid, 104–106 mp ° C.; $^1$H NMR (CDCl$_3$) δ0.97 (t, J=7.2 Hz, 3H), 1.49–1.56 (m, 2H), 1.73–1.80 (m, 2H), 2.01 (s, 3H), 2.02 (s, 3H), 2.03 (s, 3H), 2.05 (s, 3H), 2.08 (s, 3H), 2.10 (s, 3H), 2.13 (s, 3H), 3.85–3.96 (m, 2H), 3.89 (s, 3H), 3.99–4.08 (m, 4H), 4.21–4.28 (m, 2H), 4.46 (dd, J=12.3, 2.4 Hz, 1H), 4.84–4.89 (m, 2H), 5.07 (apparent t, J=10.7 Hz, 1H), 5.35–5.48 (m, 4H), 6.79 (d, J=9.0 Hz, 1H), 7.26 (m, 2H). IR (KBr) 3400, 2950, 1750, 1250 and 1050 cm$^{-1}$, mass spectrum (+FAB), m/z 876/878 (M+H), 898/900 (M+Na). Anal. Calcd. for C$_{38}$H$_{50}$ClNO$_{20}$: C, 52.09; H, 5.75; N, 1.60. Found: C, 52.26; H, 5.76; N, 1.51.

EXAMPLE 26

4-butoxy-3-chloro-N-[(4',6'-O-benzylidene)-β-D-maltosyl]-5-methoxy-benzamide Hydrate Step 1

4-butoxy-3-chloro-N-(β-D-maltosyl)-5-methoxy-benzamide Hydrate

The title compound was prepared according to the procedure of Example 4, Step 1 affording 100% as a white solid, mp decomposition at 210; $^1$H NMR (DMSO-d$_6$) 0.91 (t, 7.5 Hz, 3H), 1.41–1.50 (m, 2H), 1.70–1.77 (m, 2H), 3.06 (bt, 1H), 3.22–3.70 (m, 12H), 3.87 (s, 3H), 4.00 (apparent t, J=6.4 Hz, 3H), 4.48–4.51 (m, 2H), 6.40 (bd, J=3.5 Hz), 4.96 (apparent t, J=8.8 Hz, 1H), 5.04 (d, J=3.7 Hz, 1H), 5.11 (bs, 1H), 5.5 (bs, 1Hz), 5.56 (bs, 1 Hz), 7.51 (d, J=2.0 Hz, 1H), 7.62 (d, J=2.0, Hz, 1H), 8.93 (d, J=9.0 Hz, 1H). IR (KBr) 3300, 2900, 1600, 1550 and 1050 cm$^{-1}$, mass spectrum (+FAB), m/z 582/584 (M+H), 604/606 (M+Na). Anal. Calcd. for C$_{24}$H$_{36}$ClNO$_{13}$·0.5H$_2$O: C, 48.78; H, 6.26; N. 2.37. Found: C, 48.99; H, 6.13; N, 2.43.

Step 2

4-butoxy-3-chloro-N-[(4',6'-O-benzylidene)-β-D-maltosyl]-5-methoxy-benzamide Hydrate The title compounds were prepared according to the procedure of Example 4, Step 2 as a white solid, mp 226° C.; $^1$H NMR (DMSO-d$_6$) 0.92 (t, 7.2 Hz, 3H), 1.43–1.49 (m, 2H), 1.63–1.70 (m, 2H), 3.34–3.75 (m, 5H), 3.34–3.75 (m, 11H), 3.88 (s, 3H), 4.00 (apparent t, J=6.4 Hz, 3H), 4.12 (dd, J=9.5, 4.4 Hz, 1H), 4.63 (bs, 1H), 4.98 (apparent t, J=9.0 Hz, 1H), 5.11 (d, J=5.3 Hz, 1H), 5.16 (d, J=4.0 Hz, 1H), 5.32 (d, J=4.6 Hz, 1H), 5.57 (s, 1H), 5.60 (d, J=2.6 Hz, 1H), 5.70 (d, J=6.4 Hz, 1H), 7.35–7.38 (m, 3H), 7.43–7.46 (m, 2H), 7.52 (d, J=1.8, Hz, 1H), 7.63 (d, J=2.0 Hz, 1H), 8.94 (d, J=9.0 Hz, 1H). IR (KBr) 3400, 2900, 1650, 1550 and 1050 cm$^{-1}$, mass spectrum (+ESI) m/z 670/672 (M+H). Anal. Calcd. for C$_{31}$H$_{40}$ClNO$_{13}$·1.0 H$_2$O: C, 54.11; H, 6.15; N, 2.03. Found: C, 54.30; H, 6.10; N, 2.06.

EXAMPLE 27

N[(6-O-benzoyloxy-4',6'-O-benzylidene)-β-D-maltosyl]-4-butoxy-3-chloro-5-methoxy-benzamide The title compounds were prepared according to the procedure of Example 6 affording 64%, as a white solid, mp 217; $^1$H NMR (DMSO-d$_6$) 0.91 (t, 7.5 Hz, 3H), 1.42–1.47 (m, 2H), 1.63–1.67 (m, 2H), 3.34–3.73 (m, 8H), 3.83–3.86 (m, 4H), 3.97–4.02 (m, 3H), 4.34 (dd, J=12.0, 3.3, Hz, 1H), 4.51 (d, J=11.9 Hz, 1H), 5.07 (apparent t, J=8.8 Hz, 2H), 5.17 (d, J=3.5 Hz, 1H), 5.25 (d, J=5.7 Hz, 1H), 5.36 (d, J=5.3 Hz, 1H), 5.51 (s, 1H), 5.68 (s, 1H), 5.85 (d, J=6.4 Hz, 1H), 7.35–7.36 (m, 3H), 7.40–7.42 (m, 2H), 7.50–7.54 (m, 3H), 7.63–7.67 (m, 2H), 7.95 (d, J=8.1 Hz, 2H), 8.99 (d, J=8.8 Hz, 1H). IR (KBr) 3400, 2900, 1725, 1650, 1500, 1225 and 1050 cm$^{-1}$, mass spectrum (–FAB) m/z 772/774 (M–H). Anal. Calcd. for C$_{38}$H$_{44}$ClNO$_{14}$·0.5 H$_2$O: C, 58.27; H, 5.79; N, 1.79. Found: C, 58.24; H, 5.92; N, 1.78.

EXAMPLE 28

N-[(2,2',3,3',4',6,6'-hepta-O-acetyl-β-D-maltosyl]-4-(4-nitrilo-butoxy)-3-nitro-benzamide Step 1

4-(4-Nitrilo-butoxy)-3-nitro-benzoic acid 4-nitrilo-butyl ester

The title compound was prepared according to the procedure of Example 13, Step 1 as a yellow solid (74%), mp 60° C.; $^1$H NMR (CDCl$_3$) δ2.13–2.26 (m, 4H), 2.55 (t, J=7.2 Hz, 2H), 2.70 (t, J=6.8 Hz, 2H), 4.32 (t, J=5.7 Hz, 2H), 4.47 (t, J=6.0 Hz, 2H), 7.14 (d, J=8.8 Hz, 1H), 8.25 (dd, J=8.8, 2.2 Hz, 1H), 8.53 (d, J=2.2 Hz, 1H). IR (KBr) 3400, 2280, 1700, 1625, 1550, 1275 and 1050 cm$^{-1}$, mass spectrum (EI), m/z 317. Anal. Calcd. for C$_{15}$H$_{15}$N$_3$O$_5$: C, 56.78; H, 4.77; N, 13;.24. Found: C, 56.53; H, 4.62; N, 13.06.

Step 2

4-(4-Nitrilo-butoxy)-3-nitro-benzoic acid

The title compounds were prepared according to the procedure of Example 13, Step 2 as a light tan solid, mp 162–163° C.; $^1$H NMR (CDCl$_3$) δ2.04–2.11 (m, 2H), 2.64 (t, J=7.3 Hz, 2H), 4.30 (t, J=5.9 Hz, 2H), 7.48 (d, J=9.0 Hz, 1H), 8.16 (dd, J=8.8, 2.2 Hz, 1H), 8.35 (d, J=2.2 Hz, 1H), 13.31 (bs, 1H). IR (KBr) 3400, 3000, 2200, 1700, 1600, 1550, 1275 and 1050 cm$^{-1}$, mass spectrum (EI), m/z 250. Anal. Calcd. for C$_{11}$H$_{10}$N$_2$O$_5$: C, 52.80; H, 4.03; N, 11.20. Found: C, 52.45; H, 3 88; N, 11.03.

Step 3

N-[(2,2',3,3',4',6,6'-hepta-O-acetyl-β-D-maltosyl]-4-(4-nitrilo-butoxy)-3-nitro-benzamide The title compounds were prepared according to the procedure of Example 1, Step 2 affording 66% as a white solid, mp 110° C.; $^1$H NMR (CDCl$_3$) δ2.01 (s, 3H), 2.02 (s, 3H), 2.03 (s, 3H), 2.06 (s, 3H), 2.08 (s, 3H), 2.10 (s, 3H), 2.13 (s, 3H), 2.15–2.24 (m, 2H), 2.69 (t, J=7.0 Hz, 2H), 3.89–4.13 (m, 4H), 4.22–4.32 (m, 3H), 4.47 (dd, J=12.3, 2.4 Hz, 1H), 4.85–4.89 (m, 2H), 5.07 (apparent t, J=10.1 Hz, 1H), 5.35–5.49 (m, 5H), 6.96 (d, J=9.2 Hz, 1H), 7.14 (d, J=8.8 Hz, 1H), 7.94 (dd, J=8.8, 2.2, Hz, 1H), 8.29 (d, J=2.4 Hz, 1H). IR (KBr) 3400, 2950, 2200, 1750, 1250 and 1050 cm$^{-1}$, mass spectrum (+FAB), m/z 868 (M+H), 890 (M+Na). Anal. Calcd. for C$_{37}$H$_{45}$N$_3$O$_{12}$: C, 51.21; H, 5.23; N. 4.84. Found: C, 50.62; H, 5.15; N, 4.66.

EXAMPLE 29

N-(4',6'-O-Benzylidene-β-D-maltosyl)-4-(4-nitrilo-butoxy)-3-nitro-benzamide

Step 1

N-(β-D-maltosyl)-4-(4-nitrilo-butoxy)-3-nitro-benzamide

The title compound was prepared according, to the procedure of Example 4, Step 1 as a white solid, mp 144–145; $^1$H NMR (DMSO-d$_6$) 2.03–2.09 (m, 2H), 2.62 (t, J=7.0 Hz, 2H), 3.05 (t, J=9.2 Hz, 2H), 3.22–3.68 (m, 10H), 4.28 (t, J=5.7 Hz, 2H), 4.95 (apparent t, J=8.8 Hz, 1H), 5.04 (d, J=3.7 Hz, 1H), 7.46 (d, J=9.0 Hz, 1H), 8.17 (dd, J=9.0, 2.0, Hz, 1H), 8.46 (d, J=2.2 Hz, 1H), 9.10 (d, J=8.8 Hz, 1H). IR (KBr) 3400, 2900, 2200, 1650, 1545 and 1050 cm$^{-1}$, mass spectrum (+FAB), m/z 574 (M+H), 596 (M+Na). Anal. Calcd. for C$_{23}$H$_{31}$N$_3$N$_{14}$·0.5 H$_2$O: C, 47.42; H, 5.54; N, 7.21. Found: C, 47.41; H, 5.61; N, 7.05.

Step 2

N-(4',6'-O-Benzylidene-β-D-maltosyl)-4-(4-nitrilo-butoxy)-3-nitro-benzamide

The title compound was prepared according to the procedure of Example 4, Step 2 as a white solid (62%), mp 165–170° C.; $^1$H NMR (CD$_3$OD-d$_4$) 2.15–2.21 (m, 2H), 2.69 (t, 7.0 Hz, 2H), 3.44–3.62 (m, 5H), 3.71–3.79 (m, 3H), 3.82–3.92 (m, 3H), 4.23 (dd, J=10.1, 4.8 Hz, 1H), 4.33 (apparent t, J=5.7 Hz, 2H), 5.13–5.18 (m, 1H), 5.24 (d, J=4.0 Hz, 1H), 5.57 (s, 1H), 7.32–7.35 (m, 3H), 7.40 (d, J=9.0, Hz, 1H), 7.47–7.51 (m, 2H), 8.17 (dd, J=8.8, 2.2 Hz, 1H), 8.45 (d, J=2.4 Hz, 1H), 9.09 (d, J=8.8 Hz, 1H). IR (KBr) 3400, 2900, 2250, 1650, 1525 and 1050 cm$^{-1}$, mass spectrum (–FAB) m/z 660 (M–H). Anal. Calcd. for C$_{30}$H$_{35}$N$_3$O$_4$·0.5 H$_2$O: C, 53.73; H, 5.41; N, 6.26. Found: C, 53.51; H, 5.46; N, 6.18.

EXAMPLE 30

N-(6-O-Benzoyl-4',6'-O-benzylidene-β-D-maltosyl)-4-(4-nitrilo-butoxy)-3-nitro-benzamide The title compound was prepared according to the procedure of Example 6 as a white solid, mp 174–176° C.; $^1$H NMR (DMSO-d$_6$) 2.03–2.10 (m, 2H), 2.64 (t J=7.2 Hz, 2H), 3.28–3.76 (m, 8H), 3.85 (bm, 1H), 4.00 (dd, J=9.9, 4.8, Hz, 1H), 4.29 (apparent t, J=5.7 Hz, 1H), 4.34 (dd, J=12.3, 3.7, Hz, 1H), 4.51 (d, J=11.4, Hz, 1H), 5.09 (apparent t, J=9.0 Hz, 1H), 5.17 (d, J=4.0 Hz, 1H), 5.27 (d, J=5.7 Hz, 1H), 5.37 (d, J=5.1 Hz, 1H), 5.51 (s, 1H), 5.69 (d, J=2.0 Hz, 1H), 5.85 (d, J=6.2 Hz, 1H), 7.34–7.37 (m, 3H) 7.39–7.43 (m, 2H), 7.47–7.54 (m, 3H) 7.63–7.67 (m, 1H), 7.95 (d, J=7.0 Hz, 1H), 8.20 (dd, J=8.8, 2.2, Hz, 1H), 8.49 (d, J=2.2 Hz, 1H), 9.15 (d, J=8.8 Hz, 1H). IR (KBr) 3400, 2900, 2280, 1650, 1545, 1225, and 1070 cm$^{-1}$, mass spectrum (+FAB), m/z 788 (M+Na). Anal. Calcd. for C$_{37}$H$_{39}$ClN$_2$O$_{13}$·1.0 H$_2$O: C, 56.70; H, 5.27; N, 5.36. Found: C, 56.71; H, 5.06; N, 5.34.

EXAMPLE 31

N-(2,2',3,3'-tetra-O-Acetyl-6-O-benzoyl-4',6'-O-benzylidene-β-D-maltosyl)-4-(4-nitrilo-butoxy)-3-nitro-benzamide The title compound was prepared according to the procedure of Example 8 as a white solid (90%), mp 222–224° C.; $^1$H NMR (CDCl$_3$) 2.03 (s, 3H), 2.03 (s, 3H), 2.08 (s, 3H), 2.10 (s, 3H), 2.18–2.24 (m, 2H), 2.68 (t, J=6.8 Hz, 2H), 3.53–3.62 (m, 2H), 3.81–3.89 (m, 1H), 3.96–4.04 (m, 2H), 4.23 (apparent t, J=9.7 Hz, 1H), 4.28 (apparent t, J=5.5 Hz, 1H), 4.52 (dd, J=12.5, 3.1, Hz, 1H), 4.85–4.93 (m, 3H), 5.40 (s, 1H), 5.44–5.55 (m, 4H), 6.87 (d, J=9.0 Hz, 1H), 7.11 (d, J=8.8 Hz, 1H), 7.31–7.34 (m, 3H) 7.37–7.40 (m, 2H), 7.43–7.47 (m, 2H), 7.55–7.59 (m, 1H), 7.93 (dd, J=8.8, 2.2, Hz, 1H), 8.04–8.07 (m, 1H), 8.24 (d, J=2.4 Hz, 1H). IR (KBr) 3400, 2900, 2230, 1750, 1650, 1545, 1250, and 1070 cm$^{-1}$, mass spectrum (+FAB), m/z 956 (M+Na).

EXAMPLE 32

N-[(2,2',3,3'4',6,6'-hepta-O-acetyl-β-D-maltosyl]-3-amino-4-(4-nitrilo-butoxy)-benzamide The title compound was prepared according to the procedure of Example 2 as a white solid (86%), mp 185–187° C., $^1$H NMR (CDCl$_3$) δ2.00 (s, 3H), 2.01 (s, 3H), 2.03 (s, 3H), 2.05 (s, 3H), 2.08 (s, 3H), 2.10 (s. 3H), 2.13 (s, 3H), 2.19–2.24 (m, 2H), 2.59 (t, J=7.0 Hz, 2H), 3.84–4.07 (m, 4H), 4.15–4.29 (m, 4H), 4.44 (dd, J=12.3, 2.4 Hz, 1H), 4.85–4.90 (m, 2H), 5.07 (t, J=10.1 Hz, 1H), 5.35–5.47 (m, 4H), 6.73–6.77 (m, 2H), 7.05 (dd, J=8.35, 2.2 Hz, 1H), 7.15 (d, J=2.2 Hz, 1H). IR (KBr) 3300, 2950, 2250, 1750, 1500, 1240 and 1050 cm$^{-1}$, mass spectrum (+FAB), m/z 838 (M+H), 860 (M+Na).

EXAMPLE 33

N-[(2,2',3,3'4',6,6'-hepta-O-acetyl-β-D-maltosyl]-3-acetylamino-4-(4-nitrilo-butoxy)-benzamide The title compound was prepared according to the procedure of Example 3 as a white solid (98%), mp 213° C.; $^1$H NMR (CDCl$_3$) δ2.01 (s, 6H), 2.03 (s, 3H), 2.04 (s, 3H), 2.08 (s, 3H), 2.11 (s, 3H), 2.15 (s. 3H), 2,21 (s, 3H), 2.25–2.2 (m, 2H), 2.58–2.62 (m, 2H), 3.87–4.06 (m, 4H), 4.21–4.27 (m, 4H), 4.45 (dd, J=12.1, 2.2 Hz, 1H), 4.86–4.94 (m, 2H), 5.07 (apparent t, J=10.1 Hz, 1H), 5.35–5.49 (m, 4H), 6.88 (d, J=8.8 Hz, 1H), 7.00 (d, J=8.8 Hz, 1H), 7.60 (dd, J=8.6, 2.2 Hz, 1H), 8.08 (s, 1H), 8.76 (d, J=2.0 Hz, 1H). IR (KBr) 3400, 2950, 2250, 1750, 1245 and 1050 cm$^{-1}$, mass spectrum (+FAB), m/z 880 (M+H), 902 (M+Na). Anal. Calcd. for C$_{39}$H$_{49}$N$_3$O$_{20}$: C, 53.24; H, 5.61; N, 4.78. Found: C, 52.83; H, 5.49; N, 4.67.

EXAMPLE 34

3-Acetylamino-N-(6-O-benzoyl-4',6'-O-benzylidene-β-D-maltosyl)-4-(4-nitrilo-butoxy)-benzamide The title compound was prepared according to the procedure of Example 6 as a white solid (92%), mp 238° C.; $^1$H NMR (DMSO-d$_6$) 2.05–2.09 (m, 5H), 2.75 (t, J=7.0 Hz, 2H), 3.33–3.40 (m, 1H), 3.50–3.66 (m, 7H), 3.70–3.85 (bm, 1H), 4.01 (dd, J=9.9, 4.8, Hz, 1H), 4.13 (apparent t, J=5.1 Hz, 1H), 4.34 (dd, J=12.3, 3.7, Hz, 1H), 4.50 (d, J=11.0, Hz, 1H), 5.08 (apparent t, J=8.8 Hz, 1H), 5.13–5.16 (m, 2H), 5.36 (d, J=5.3 Hz, 1H), 5.51 (s, 1H), 5.65 (d, J=1.8 Hz, 1H), 5.85 (d, J=6.2 Hz, 1H), 7.08 (d, J=8.6 Hz, 1H), 7.35–7.37 (m, 3H) 7.40–7.43 (m, 2H), 7.50–7.54 (m, 2H), 7.63–7.70 (m, 2H), 7.94–7.96 (m, 2H), 8.41 (s, Hz, 1H), 8.80 (d, J=9.0 Hz, 1H), 8.99 (s, 1H). IR (KBr) 3400, 2900, 2280, 1650, 1545, 1225, and 1070 cm$^{-1}$, mass spectrum (+ESI), m/z 778 (M+H), (−ESI), m/z 776 (M−H). Anal. Calcd. for C$_{39}$H$_{43}$N$_3$O$_{14}$·1.5 H$_2$O: C, 58.21; H, 5.76; N, 5.22. Found: C, 58.21; H, 5.64; N, 5.24.

EXAMPLE 35

N-(Hepta-O-acetyl-β-D-maltosyl)-6-chloropyridine-3-carboxamide

The title compound was prepared according to the procedure of Example 1, Step 2 affording a white solid, mp 190° C.; $^1$H NMR (CDCl$_3$) δ2.01 (s, 3H), 2.02 (s, 3H), 2.03 (s, 3H), 2.05 (s, 3H), 2.08 (s, 3H), 2.10 (s, 3H), 2.13 (s, 3H), 3.86–3.96 (m, 2H), 4.00–4.07 (m, 2H), 4.21–4.29 (m, 2H), 4.47 (dd, J=12.3, 2.4 Hz, 1H), 4.84–4.89 (m, 2H), 5.07 (apparent t, J=10.1 Hz, 1H), 5.34–5.49 (m, 4H), 6.99 (d, J=8.8 Hz, 1H), 7.42 (dd, J=8.3, 0.7 Hz, 1H), 8.02 (dd, J=8.3, 2.6, Hz, 1 H), 8.73 (dd, J=2.6, 0.7 Hz, 1H). IR (KBr) 3400, 2950, 1750, 1250 and 1050 cm$^{-1}$, mass spectrum (+FAB), m/z 775 (M+H), 797 (M+Na). Anal. Calcd. for C$_{32}$H$_{39}$N$_2$O$_{18}$Cl·1.0 H$_2$O: C, 48.46; H, 5.21; N, 3.53. Found: C, 48.60; H, 4.95; N, 3.45.

EXAMPLE 36

N-(Hepta-O-acetyl-β-D-maltosyl)-2,6-dimethoxy-pyridine-3-carboxamide

The title compound was prepared according to the procedure of Example 1, Step 2 affording a white solid, mp 125–130° C.; $^1$H NMR (CDCl$_3$) δ1.98 (s, 3H), 2.00 (s, 3H), 2.03 (s, 6H), 2.08 (s, 3H), 2.10 (s, 3H), 2.13(s,3H), 3.86–3.99 (m, 2H), 3.96 (s, 3H), 4.01–4.06 (m, 2H), 4.07 (s, 3H), 4.22–4.30 (m, 2H), 4.42 (dd, J=12.3, 2.6 Hz, 1H), 4.87 (dd, J=10.5, 4.0 Hz, 1H), 4.99 (apparent t, J=9.4 Hz, 1H), 5.06 (apparent t, J=9.7 Hz, 1H), 5.35–5.49 (m, 4H), 6.45 (d, J=8.3 Hz, 1H), 8.35 (d, J=8.4 Hz, 1H), 8.37 (d, J=8.8, Hz, 1H). IR (KBr) 3400, 2950, 1750, 1400, 1250 and 1050 cm$^{-1}$, mass spectrum (+FAB), m/z 801 (M+H), 823 (M+Na). Anal. Calcd. for C$_{34}$H$_{44}$N$_2$O$_2$O·0.5 H$_2$O: C, 50.43; H, 5.60; N, 3.46. Found: C, 50.64; H, 5.52; N, 3,32.

EXAMPLE 37

N-(Hepta-O-acetyl-β-D-maltosyl)-5-bromopyridine-3-carboxamide

The title compound was prepared according to the procedure of Example 1, Step 2 affording a white solid, mp 167–170° C.; $^1$H NMR (CDCl$_3$) δ2.01 (s, 3H), 2.03 (s, 6H), 2.06 (s, 3H), 2.08 (s, 3H), 2.10 (s, 3H), 2.13 (s, 3H), 3.86–4.00 (m, 2H), 4.02–4.07 (m, 2H), 4.22–4.28 (m, 2H), 4.47 (dd, J=12.3, 2.4 Hz, 1H), 4.85–4.90 (m, 2H), 5.07 (apparent t, J=9.7 Hz, 1H), 5.35–5.49 (m, 4H), 7.03 (d, J=9.0 Hz, 1H), 8.25 (t, J=2.2 Hz, 1H), 8.83 (s, 1H). IR (KBr) 3300, 2950, 1750, 1250 and 1050 cm$^{-1}$, mass spectrum (+FAB), m/z 819/821 (M+H), 841/843 (M+Na). Anal. Calcd. for C$_{32}$H$_{39}$N$_2$O$_{18}$Br: C, 46.90; H, 4.80; N, 3.42. Found: C, 46.77; H, 4.82; N, 3.14.

EXAMPLE 38

N-(Hepta-O-acetyl-β-D-maltosyl)-3-(trifluoromethyl)-benzamide

The title compound was prepared according to the procedure of Example 10 affording a white solid, mp 109–111° C.; $^1$H NMR (CDCl$_3$) δ2.01 (s, 3H), 9.02 (s, 3H), 2.03 (s, 3H), 2.06 (s, 3H), 2.08 (s, 3H), 2.10 (s, 3H), 2.13 (s, 3H), 3.88–3.96 (m, 2H), 4.02–4.07 (m, 2H), 4.21–4.29 (m, 2H), 4.46 (dd, J=12.3, 2.4 Hz, 1H), 4.86–4.91 (m, 2H), 5.07 (t, J=10.1 Hz, 1H), 5.35–5.50 (m, 4H), 6.96 (d, J=9.0 Hz, 1H), 7.59 (t, J=7.7 Hz, 1H), 7.80 (d, J=7.7 Hz, 1H), 7.88 (d, J=7.9 Hz, 1H) 8.05 (s, 1H). IR (KBr) 3400, 2930, 1750, 1550, 1245 and 1050 cm$^{-1}$, mass spectrum (+FAB), m/z 808 (M+H), 830 (M+Na). Anal. Calcd. for C$_{34}$H$_{40}$F$_3$NO$_{18}$: C, 50.56; H,4.99; N,1.73. Found: C, 49.97; H,4.87; N, 1.68.

EXAMPLE 39

N-(4',6'-O-Benzylidene-β-D-maltosyl)-3-(trifluoromethyl)-Benzamide

Step 1

N-(β-D-Maltosyl)-3-(trifluoro-methyl)-benzamide

The title compound was prepared according to the procedure of Example 4, Step 1 affording a white solid, mp 158–159° C.; $^1$H NMR (DMSO-$_6$) δ3.06 (apparent t, J=9.0 Hz, 2H), 3.21–3.71 (m, 17H), 4.97 (d, J=3.7 Hz, 1H), 5.01 (d, J=8.88 Hz, 1H), 7.63 (t , J=7.7 Hz, 1H), 7.79 (d, J=7.7 Hz, 1H), 8.19 (d, J=7.9 Hz, 1H), 8.26 (s, 1H). IR (KBr) 3400, 2930, 1675, 1550, 1350 and 1075 cm$^{-1}$, mass spectrum (+FAB), m/z 514 (M+H), 536 (M+Na). Anal. Calcd. for C$_{20}$H$_{26}$F$_3$NO$_{11}$·2H$_2$O: C,43.72; H, 5.50; N, 2.55. Found: C, 43.38; H, 5.06; N, 2.4.

Step 2

N-(4',6'-O-Benzylidene-β-D-maltosyl)-3-(trifluoromethyl)-Benzamide

The title compound was prepared according to the procedure of Example 4 Step 2 affording a white solid, mp 230° C. decomposed; $^1$H NMR (DMSO-d$_6$) 3.32–3.48 (m, 4H), 3.50–3.60 (m, 4H), 3.61–3.78 (m, 3H), 4.67 (bs, 1H), 5.02 (t, J=9.0 Hz, 1H), 5.15–5.17 (m, 2H), 5.32 (d, J=0.6 Hz, 1H), 5.58 (s, 1H), 5.61 (d, J=2.2 Hz, 1H), 5.71 (d, J=6.4 Hz, 1H), 7.32–7.40 (m, 3H), 7.41–7.47 (m, 2H), 7.74 (t, J=7.9 Hz, 1H), 7.92 (d, J=7.7 Hz, 1H), 8.21 (d, J=7.7 Hz, 1H), 8.28 (s, 1H), 9.2 (d, J=8.8 Hz, 1H). IR (KBr) 3400, 2930, 1700, 1550, 1255, and 1075 cm$^{-1}$, mass spectrum (+FAB), m/z 602 (M+H), 624 (M+Na). Anal. Calcd. for C$_{27}$H$_{30}$F$_3$NO$_{11}$. 0.5 H$_2$O: C, 53.12; H, 5.08; N, 2.29. Found: C, 52.82; H, 5.05; N, 2.41.

EXAMPLE 40

N-[{6-O-Benzoyl-4',6'-O-benzylidene}-β-D-maltosyl]-3-(trifluoromethyl)-benzamide The title compound was prepared according to the procedure of Step 6 affording a white solid, mp 190° C. decomposed; $^1$H NMR (DMSO-d$_6$) δ3.28–3.76 (m, 8H), 3.86 (bs, 1H), 4.01 (dd, J=9.9, 4.6 Hz, 1H), 4.30 (dd, J=12.3, 4.0 Hz, 1H), 4.51 (d, J=11.4 Hz, 1H), 5.17 (aparant t, J=3.7 Hz, 1H), 5.29 (d, J=5.5 Hz, 1H), 5.37 (d, J=5.1 Hz, 1H), 5.51 (s, 1H), 5.69 (d, J=2.0Hz, 1H), 5.87 (d, J=5.9Hz, 1H), 7.33–7.40 (m, 3H), 7.41–7.43 (m, 2H), 7.52 (t, J=7.7 Hz, 2H), 7.65 (t, J=7.5 Hz, 1H), 7.72 (t, J=7.9, Hz, 1H), 7.92 (d, J=7.1 Hz, 1H), 7.95 (d, J=7.3 Hz, 1H), 8.24 (d, J=2.2 Hz, 1H), 8.27 (s, 1H), 9.26 (d, J=8.8 Hz, 1H).IR (KBr) 3400, 2930, 1735, 1550, 1300, and 1075 cm$^{-1}$, mass spectrum (+FAB), m/z 706 (M−H), 728 (M+Na). Anal. Calcd. for $C_{34}H_{34}F_3NO_{12}$.0.5 $H_2O$: C, 57.14; H, 4.94; N, 1.96. Found: C, 57.29; H, 4.88; N, 1.99.

EXAMPLE 41

N-(Hepta-O-acetyl-β-D-maltosyl)-6-methylpyridine-3-carboxamide

The title compound was prepared according to the procedure of Example 1 Step 2 affording a white solid, mp 115° C.; $^1$H NMR (CDCl$_3$) δ2.01 (s, 6H), 2.0.3 (s, 3H), 2.05 (s, 3H), 2.08 (s, 3H), 2.10 (s, 3H), 2.13 (s, 3H), 2.63 (s, 3H), 3.86–4.00 (m, 2H), 4.02–4.11 (m, 2H), 4.21–4.29 (m, 2H), 4.46 (dd, J=12.1, 2.6 Hz, 1H), 4.85–4.91 (m, 2H), 5.07 (apparent t, J=10.1 Hz, 1H), 5.34–5.48 (m, 4H), 7.03 (d, J=8.6 Hz, 1H), 7.30 (d, J=7.9 Hz, 1H), 7.97 (dd, J=8.1, 2.4 Hz, 1H), 8.86 (d, J=2.0 Hz, 1H). IR (KBr) 3400, 2950, 1750, 1250 and 1050 cm$^{-1}$, mass spectrum (+FAB), m/z 755 (M+H), 777 (M+Na). Anal. Calcd. for $C_{33}H_{42}N_{22}O_{18}$. 0.5: C, 51.90; H, 5.68; N, 3.67. Found: C, 51.99; H, 5.63; N, 3.55.

EXAMPLE 42

4-Butoxy-3,5-dichloro-N-β-D-maltosyl-benzamide

The title compound was prepared according to the procedure of Example 4, Step 1 affording a white solid, mp 210° C. decomposed; $^1$H NMR (DMSO d6) δ0.94 (t, J=7.3 Hz, 4H), 1.47–1.52 (m, 2H), 1.72–1.79 (m, 2H), 3.02–3.07 (m, 1H), 3.22–3.70 (m, 11H), 4.04 (t, J=6.4 Hz, 2H), 4.46–4.52 (m, 2H), 4.88–4.95 (m, 3H), 5.04 (d, J=3.7 Hz, 1H), 5.13 (d, J=5.5 Hz, 1H), 5.48 (d, J=5.9 Hz, 1H), 5.59 (d, J=3.8 Hz, 1H), 8.01 (s, 2H), 9.06 (d, J=8.8 Hz, 1H). IR (KBr) 3400, 2930, 1600, 1550, and 1075 cm$^{-1}$, mass spectrum (+FAB), m/z 586/588/590 (M+H), 608/610/612 (M+Na). Anal. Calcd. for $C_{23}H_{33}Cl_2NO_{12}$: C, 47.11; H, 5.67; N, 2.39 Found: C, 46.78; H, 5.74; N, 2.39.

EXAMPLE 43

N-(4',6'-O-Benzylidene-β-D-maltosyl)-4-butoxy-3,5-dichloro-benzamide

The title compound was prepared according to the procedure of Example 4, Step 2 affording a white solid, mp 105–107° C.; $^1$H NMR (DMSO) δ0.94 (t, J=7.5 Hz, 3H), 1.47–1.53 (m, 2H), 1.72–1.77 (m, 2H), 3.34–3.41 (m, 4H), 3.48–3.61 (m, 9H), 3.64–3.74 (m, 3H), 4.04 (t, J=6.4 Hz, 2H), 4.12 (dd, J=9.2, 4.2 Hz, 1H), 4.95 (t, J=8.8 Hz, 1H), 5.16 (d, J=3.7 Hz, 1H), 5.57 (s, 1H), 7.36–7.38 (m, 3H), 7.43–7.46 (m, 2H), 8.02 (s, 2H), 9.09 (d, J=8.8 Hz, 1H). IR (KBr) 3400, 2930, 1550, 1450, 1350, 1255 and 1075 cm$^{-1}$, mass spectrum (+FAB), m/z 696/698 (M+Na). Anal. Calcd. for $C_{30}H_{37}Cl_2NO_{12}$.1.5 $H_2O$: C, 51.36; H, 5.75; N, 2.00. Found: C, 51.25; H, 5.46; N, 2.12.

EXAMPLE 44

N-(Hepta-O-acetyl-β-D-maltosyl)-3-chloro-4-methoxy-benzamide

The title compound was prepared according to the procedure of Example 10 affording a white solid, mp 106–110° C.; $^1$H NMR (CDCl$_3$) δ2.01 (s, 6H), 2.03 (s, 3H), 2.05 (s, 3H), 2.08 (s, 3H), 2.10 (s, 3H), 2.13 (s, 3H), 3.86–4.07 (m, 4H), 3.95 (s, 3H), 4.21–4.29 (m, 2H), 4.45 (dd, J=12.3, 2.4 Hz, 1H), 4.85–4.90 (m, 2H), 5.07 (apparent t, J=10.1 Hz, 1H), 5.35–5.48 (m, 4H), 6.78 (d, J=9.2 Hz, 1H), 6.86 (d, J=8.6 Hz, 1H), 7.61 (dd, J=8.6, 2.2 Hz, 1H), 7.81 (d, J=2.2 Hz, 1H). IR (KBr) 3400, 2950, 1750, 1250 and 1050 cm$^{-1}$, mass spectrum (+ESI), m/z 804 (M+H), 821.1 (M+NH$_4$).

EXAMPLE 45

N-(2,2',3,3',4',6,6'-hepta-O-acetyl-β-D-maltosyl)-1-(3,4-dimethoxy)-phenyl-acetamide The title compound was prepared according to the procedure of Example 10 affording a white solid, mp 95–97° C.; $^1$H NMR (CDCl$_3$) δ1.83 (s, 3H), 1.98 (s, 3H), 1.99 (s, 6H), 2.02 (s, 3H), 2.04 (s, 3H), 2.09 (s, 3H), 2.12 (s, 3H), 3.47 (ABq, J=15.6, .δ=0.03, 2H), 3.75–3.79 (m, 1H), 3.87–3.94 (m, 7H), 4.02 (dd J=12.3, 2.4 Hz, 1H), 4.20 (t, J=3.5 Hz, 1H), 4.23 (t, J=3.7 Hz, 1H), 4.41 (dd, J=10.5, 3.9 Hz, 1H), 5.04 (t, J=9.7 Hz, 1H), 5.21 (aparant t, J=9.7 Hz, 1H), 5.29–5.36 (m, 3H), 6.06 (d, J=9.2 Hz, 1H), 6.71–6.75 (m, 2 1H), 6.83 (d, J=8.12 Hz, 1H). IR (KBr) 3400, 2930, 1750, 1530, 1245 and 1050 cm$^{-1}$, mass spectrum (+FAB), m/z 814 (M+H), 836 (M+Na).

EXAMPLE 46

N-(4',6'-Benzylidene-β-D-maltosyl)-2-(3,4-dimethoxy-phenyl)-acetamide

Step 1

N-(β-D-maltosyl)-2-(3,4-dimethoxy-phenyl)acetamide

The title compound was prepared according to the procedure of Example 4, Step 1 affording a white solid, mp 210–213° C.; $^1$H NMR (DMSO-d$_6$) δ3.02–3.64 (m, 20H), 4.72 (t, J=9.0 Hz, 1H), 5.01 (d, J=3.7 Hz, 1H), 6.75 (dd, J=8.3, 1.7 Hz, 1H), 6.83–6.88 (m, 2H), 8.57 (d, J=9.2 Hz, 1H). IR (KBr) 3400, 2930, 1675, 1530, 1265 and 1050 cm$^{-1}$, mass spectrum (-FAB), m/z 518 (M-H). Anal. Calcd. for $C_{22}H_{33}NO_{13}$: C, 50.87; H, 6.40; N, 2.70. Found: C, 50.59; H, 6.44; N, 2.60.

Step 2

N-(4',6'-Benzylidene-β-D-maltosyl)-2-(3,4-dimethoxyphenyl)-acetamide

The title compound was prepared according to the procedure of Example 4, Step 2 affording a white solid, mp 200–205 dec. ° C.; $^1$H NMR (DMSO-d6) δ3.13–3.70 (m, 19H), 4.10 (dd, J=9.0, 4.0 Hz, 1H), 4.60 (aparant t, J=5.5 Hz, 1H), 4.74 (aparant t, J=9.0Hz, 1H), 5.01 (d, J=6.2 Hz, 1H), 5.14 (d, J=3.7 Hz, 1H), 5.31 (d, J=5.3 Hz, 1H), 5.55 (d, J=4.6 Hz, 2H), 5.70 (d, J=6,6 Hz, 1H), 6.76 (dd, J=8.1, 1.8 Hz, 1H), 6.83–6.89 (m, 2H), 7.34–7.36 (m, 3H), 7.42–7.45 (m, 2H), 8.58 (d, J=9.2 Hz, 1H). IR (KBr) 3400, 2930, 1750, 1550, 1245 and 1075 cm$^{-1}$, mass spectrum (-FAB), m/z 606 (M-H).

EXAMPLE 47

N-(6-O-Benzoyl-4',6'-O-benzylidene-β-D-maltosyl)-2-(3,4-dimethoxy-phenyl)-acetamide The title compound was prepared according to the procedure of Example 6 affording a white solid, mp 205–207° C.; $^1$H NMR (DMSO-d6) δ3.28–3.50 (m, 5H), 3.52–3.68 (m, 5H), 3.71–3.97 (m, 1H), 3.67 (s, 3H), 3.69 (s, 3H), 3.99 (dd, J=9.9, 4.8 Hz, 1H), 4.30 (dd, J=12.3, 4.20 Hz, 1H), 4.46 (d, J=5.1 Hz, 1H), 4.85 (aparant t, J=9.0Hz, 1H), 5.14 (d, J=4.6Hz, 2H), 5.34 (d, J=5.1 Hz, 1H), 5.50 (s, 1H), 5.62 (d, J=2.6 Hz, 1H), 5.84 (d, J=6.2 Hz, 1H), 6.74 (dd, J=8.3, 2.0 Hz, 1H), 6.80 (d, J=8.1 Hz, 1H), 6.86 (d, J=2.0 Hz, 1H), 7.33–7.50 (m, 5H), 7.52 (t, J=7.9 Hz, 1H), 7.63–7.67 (m, 2H), 7.95 (dd, J=7.0, 1.3 Hz, 2H), 8.66 (d, J=9.0 Hz, 1H).

IR (KBr) 3400, 2930, 1750, 1550, 1245 and 1075 cm$^{-1}$, mass spectrum (+ESI), m/z 712 (M+H), 734 (M+Na). Anal.

Calcd. for $C_{36}H_{41}NO_{14} \cdot 1.5 H_2O$: C, 58.53; H, 5.87; N, 1.90. Found: C, 58.93; H, 5.77; N, 1.78.

EXAMPLE 48

N-(Hepta-O-acetyl-β-D-maltosyl)-2-(4-hydroxy-3-nitro-phenyl)-acetamide

The title compound was prepared according to the procedure of Example 13, Step 3 affording a white solid. mp 106° C.; $^1H$ NMR (CDCl$_3$) δ1.93 (s, 3H), 2.00 (s, 3H), 2.01 (s, 3H), 2.02 (s, 3H), 2.05 (s, 3H), 2.09 (s, 3H), 2.13 (s, 3H), 3.51 (ABq, J=15.8 Hz, Δδ=0.30, 2H), 3.76–3.80 (m, 1H), 3.89–3.96 (m. 2H) 4.03 (dd, J=12.5, 2.2 Hz, 1H), 4.22 (dd, J=12.5, 4.0 Hz, 1H), 4.43 (dd, J=12.3, 2.2 Hz, 1H), 4.67 (apparent t, J=9.7 Hz, 1H), 5.05 (apparent t, J=10.1 Hz, 1H), 5.20 (apparent t, J=9.2 Hz, 1H), 5.32–5.38 (m, 3H), 6.15 (d, J=9.0 Hz, 1H), 7.15 (d, J=8.6 Hz, 1H), 7.46 (dd, J=8.6, 2.0 Hz, 1H), 7.95 (d, J=2.0 Hz, 1H), 10.5 (d, J=0.4 Hz, 1H). IR (KBr) 3400, 2950, 1750, 1250 and 1050 cm$^{-1}$, mass spectrum (+FAB), m/z 815 (M+H), 837 (M+Na).

EXAMPLE 49

N-(2,2',3,3',4',6,6'-Hepta-O-acetyl-β-D-maltosyl)-4-butoxy-3,5-dichloro-benzylamide The title compound was prepared according to the procedure of Example 10 affording a white solid, mp 104–105° C.; $^1H$ NMR (CDCl$_3$) δ0.99 (t, J=7.5 Hz, 3H), 1.52–1.60 (m, 2H), 1.81–1.87 (m, 2H), 2.01 (s, 3H), 2.03 (s, 6H), 2.06 (s, 3H), 2.08 (s, 3H), 2.10 (s, 3H), 2.13 (s, 3H), 3.84–3.94 (m, 2H), 3.95–4.08 (m, 5H), 4.22–4.27 (m, 2H), 4.46 (dd, J=12.1, 2.4 Hz, 1H), 4.83–4.89 (m, 2H), 5.07 (apparent t, J=9.4 Hz, 1H), 5.34–5.47 (m, 3H), 6.77 (d, J=9.23 Hz, 1H), 7.78 (s, 2H). IR (KBr) 3400, 2930, 1750, 1550, 1325, 1245 and 1075 cm$^{-1}$, mass spectrum (+FAB), m/z 880/882/884 (M+H), 902/904/906 (M+Na). Anal. Calcd. for $C_{37}H_{47}Cl_2NO_{19}$: C, 50.46; H, 5.38; N, 1.59. Found: C, 50.01; H, 5.39; N, 1.58.

EXAMPLE 50

N-(2,2',3,3',4',6,6'-hepta-O-acetyl-β-D-maltosyl)-2-(4-chloro-3-nitro-phenyl)-acetamide The title compound was prepared according to the procedure of Example 13, Step 3 affording a white solid, mp 103° C.; $^1H$ NMR (CDCl$_3$) δ1.93 (s, 3H), 2.00 (s, 3H), 2.01 (s, 3H), 2.02 (s, 3H), 2.06 (s, 3H), 2.09 (s, 3H), 2.13 (s, 3H), 3.51 (q, J=15.2 Hz, 2H), 3.76–3.80 (m, 1H), 3.90–3.97 (m, 2H), 4.04 (dd, J=12.5, 2.2 Hz, 1H), 4.20–4.24 (m, 2H), 4.44 (dd, J=12.1, 2.4 Hz, 1H), 4.69 (apparent t, J=9.4 Hz, 1H), 4.85 (dd, J=10.5, 4.2 Hz, 1H), 5.05 (apparent t, J=10.1 Hz, 1H), 5.20 (apparent t, J=9.2 Hz, 1H), 5.32–5.38 (m, 3H), 6.23 (d, J=9.0 Hz, 1H), 7.41 (dd, J=8.3, 2.2 Hz, 1H), 7.53 (d, J=8.1 Hz, 1H), 7.75 (d, J=2.0 Hz, 1H). IR (KBr) 3400, 2950, 1750, 1245 and 1050 cm$^{-1}$, mass spectrum (+FAB), m/z 833 (M+H), 855 (M+Na). Anal. Calcd. for $C_{34}H_{41}ClN_2O_{20}$: C, 49.02; H, 4.96; N, 3,36. Found: C, 48.67; H, 5.06; N, 3.19.

EXAMPLE 51

2-[3-Acetyl-amino)-4-chloro-phenyl]-N-(6-O-benzoyl-4',6'-O-benzylidene-β-D-maltosyl)-acetamide The title compound was prepared according to the procedure of Example 6 affording a white solid, $^1H$ NMR (DMSO-d6) δ2.05 (s, 3H), 3.21–3.75 (m, 11H), 3.99 (dd, J=9.9, 4.8 Hz, 1H), 4.31 (dd, J=12.3, 4.0 Hz, 1H), 4.45 (d, J=10.8 Hz, 1H), 4.84 (apparent t, J=9.0 Hz, 1H), 5.13–5.15 (m, 2H), 5.34 (d, J=5.3 Hz, 1H), 5.50 (s, 1H), 5.63 (d, J=2.6Hz, 1H), 5.83 (d, J=6.2 Hz, 1H), 7.06 (dd, J=8.3, 2.0 Hz, 1H), 7.33–7.42 (m, 6H), 7.49–7.56 (m, 3H), 7.63–7.68 (m, 1H), 7.95 (dd, J=8.6, 1.1 Hz, 2H), 8.74 (d, J=9.0 Hz, 1H), 9.45 (s, 1H).

IR (KBr) 3400, 2930, 1750, 1550, 1245 and 1075 cm$^{-1}$, mass spectrum (+FAB), m/z 765/767 (M+Na).

What is claimed is:

1. A compound of formula I having the structure

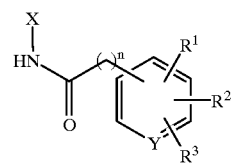

I wherein
Y is C or N;
where n is 0–3;
X is

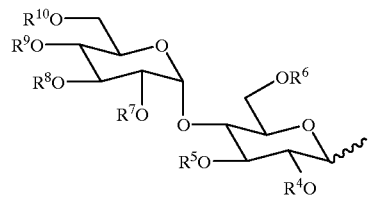

$R^1$, and $R^2$ are each independently, hydrogen, alkyl of 1 to 6 carbon atoms, halo, acetyl, phenyl, $CF_3$, CN, OH, $NO_2$, $NH_2$, alkoxy of 1 to 6 carbon atoms, or cyanoalkoxy of 2 to 7 carbon atoms;

$R^3$ is hydrogen, acylamide of 2 to 6 carbon atoms or alkoxy of 1 to 6 carbon atoms;

$R^4$, $R^5$, $R^6$, $R^7$, and $R^8$ are each, independently, acyl of 1 to 6 carbon atoms, benzyl substituted with $R^1$, and $R^2$; or benzoyl substituted with $R^1$ and $R^2$;

$R^9$ and $R^{10}$ are each, independently, acyl of 1 to 6 carbon atoms, or the $R^9$ and $R^{10}$ groups on the 4' and 6' positions of the maltose may be taken together to form a cyclic acetal which may be substituted with alkyl of 1 to 6 carbon atoms, two alkyl groups each having 1 to 6 carbon atoms, pyridine substituted with $R^1$, phenyl substituted with $R^1$, benzyl substituted with $R^1$, 2-phenylethyl substituted with $R^1$, or 3-phenylpropyl substituted with $R^1$;

with the provisio that when $R^1$ or $R^2$ are cyanoalkoxy of 2–7 carbon atoms, $R^3$ is not acylamide, and further provided that when $R^1$, $R^2$, or $R^3$ are alkoxy of 1–6 carbon atoms, at least one of $R^1$, $R^2$, $R^3$, or $R^4$ are not hydrogen;

or a pharmaceutically acceptable salt thereof.

2. The compound according to claim 1, wherein
n is 0–1;
$R^1$, and $R^2$ are each independently, hydrogen, halogen, $CF_3$, OH, $NO_2$, $NH_2$, methoxy, butoxy, or butoxynitrile;
$R^3$ is hydrogen, acetamide, or methoxy;
$R^4$, $R^5$, $R^6$, $R^7$, and $R^8$ are each, independently, hydrogen, an acyl of 1–6 carbon atoms, or benzoyl;

$R^9$ and $R^{10}$ are each, independently, acyl of 1–6 carbon atoms, or the $R^9$ and $R^{10}$ groups on the 4' and 6' positions of the maltose are taken together form a benzylidene ring;

or a pharmaceutically acceptable salt thereof.

3. The compound of claim 2, wherein n is 0;

$R^1$, and $R^2$ are each independently, hydrogen or halogen;

$R^3$ is hydrogen;

or a pharmaceutically acceptable salt thereof.

4. The compound of claim 1, which is (R)-3-(acetylamino)-N-[6-O-benzoyl-4-O-[4,6-O-(phenylmethylene)-(α-D-glucopyranosyl]-β-D-glucopyranosyl]-4-chlorobenzamide or a pharmaceutically acceptable salt thereof.

5. The compound of claim 1, which is 4-chloro-N-[(2,2', 3,3'-tetra-O-acetyl-6-benzoyl-4',6'-O-benzylidene)-β-D-maltosyl]-3-nitro-benzamide.

6. The compound of claim 1, which is (R)-N-[2-O-acetyl-4-O-[2-O-acetyl-4,6-O-(phenylmethylene)-α-D-glucopyranosyl]-6-O-benzoyl-β-D-glucopyranosyl]-3-(acetylamino)-4-chlorobenzamide chlorobenzamide or a pharmaceutically accept acceptable salt thereof.

7. The compound of claim 1, which is N-(6-O-benzoyl-4',6'-O-benzylidene-β-D-maltosyl)-3-chloro-4-(4-nitrilo-butoxy)-phenyl amide chlorobenzamide or a pharmaceutically acceptable salt thereof.

8. The compound of claim 1, which is N-(6-O-benzoyl-4',6'-O-benzylidene-β-D-maltosyl)-4-chloro-3-methoxy-benzamide chlorobenzamide or a pharmaceutically acceptable salt thereof.

9. The compound of claim 1, which is N-(6-O-benzoyl-4',6'-O-benzylidene-β-D-maltosyl)-4-(4-nitrilo-butoxy)-3-nitro-benzamide chlorobenzamide or a pharmaceutically acceptable salt thereof.

10. The compound of claim 1, which is 3-acetylamino-N-(6-O-benzoyl-4',6'-O-benzylidene-β-D-maltosyl)-4-(4-nitrilo-butoxy)-benzamide chlorobenzamide or a pharmaceutically acceptable salt thereof.

11. The compound of claim 1, which is N-(hepta-O-acetyl-β-D-maltosyl)-3-chloro-4-methoxy-benzamide.

12. The compound of claim 1, which is N-(6-O-benzoyl-4',6'-O-benzylidene-β-D-maltosyl)-2-(3,4-dimethoxy-phenyl)-acetamide chlorobenzamide or a pharmaceutically acceptable salt thereof.

13. The compound of claim 1, which is 2-[3-acetyl-amino)-4-chloro-phenyl]-N-(6-O-benzoyl-4',6'-O-benzylidene-β-D-maltosyl)-acetamide chlorobenzamide or a pharmaceutically acceptable salt thereof.

14. The compound of claim 1, which is:

a) N-(hepta-O-acetyl-1-deoxy-β-D-maltosyl)-4-chloro-3-nitro-benzamide;

b) 3-amino-4-chloro-N-[2,3,6-tri-O-acetyl-4-O-(2,3,4,6-tetra-O-acetyl-α-D-glucopyranosyl)-β-D-glucopyranosyl}-benzamide;

c) 3-(acetylamino)-4-chloro-N-[2,3,6-tri-O-acetyl-4-O-(2,3,4,6-tetra-O-acetyl-α-D-glucopyranosyl)-β-D-glucopyranosyl}-benzamide;

d) (R)-3-(acetylamino)-4-chloro-N-[4-O-[4,6-O-(phenylmethylene)-α-D-glucopyranosyl]-β-D-glucopyranosyl]-benzamide or a pharmaceutically acceptable salt thereof;

e) (R)-4-chloro-3-nitro-N-[4-O-[4,6-O-(phenylmethylene)-α-D-glucopyranosyl]-β-D-glucopyranosyl]-benzamide or a pharmaceutically acceptable salt thereof;

f) (R)-4-chloro-N-[(6-O-benzoyl-4',6'-O-benzylidene)-β-D-maltosyl]-3-nitro-benzamide or a pharmaceutically acceptable salt thereof;

g) N-(Hepta-O-acetyl-β-D-maltosyl)-4-chloro-benzamide;

h) N-(4',6'-O-benzylidene-β-D-maltosyl)-4-chloro-benzamide or a pharmaceutically acceptable salt thereof;

i) N-(6-O-benzoyl-4',6'-O-benzylidene-β-D-maltosyl)-4-chloro-benzamide or a pharmaceutically acceptable salt thereof;

j) N-[(2,2',3,3'4',6,6'-hepta-O-acetyl-β-D-maltosyl]-3-chloro-4-nitrilobutoxy-benzoic acid amide;

k) N-[(2,2',3,3'4',6,6'-hepta-O-acetyl-α-D-maltosyl]-3-chloro-4-nitrilobutoxy-benzoic acid amide;

l) N-(4',6'-O-benzylidene-β-D-maltosyl)-3-chloro-4-(4-nitrilo-butoxy)-benzamide or a pharmaceutically acceptable salt thereof;

m) N-(2,2',3,3'-tetra-O-acetyl-6-O-benzoyl-4',6'-O-benzylidene-β-D-maltosyl)-3-chloro-4-(4-nitrilo-butoxy)-benzamide;

n) 4-butoxy-3-chloro-N-[2,3,6-tri-O-acetyl-4-O-(2,3,4,6-tetra-O-acetyl-α-D-glucopyranosyl)-β-D-glucopyranosyl]benzamide;

o) 4-butoxy-3-chloro-N-[(6-O-benzoyl-4',6'-O-benzylidene)-β-D-maltosyl]-benzamide or a pharmaceutically acceptable salt thereof;

p) 4-butoxy-3-chloro-N-[(2,3,2',3'-tetra-O-acetyl-6-O-benzoyl-4',6'-O-benzylidene)-β-D-maltosyl]-benzamide;

q) 4-chloro-3-methoxy-N-[2,3,6-tri-O-acetyl-4-O-(2,3,4,6-tetra-O-acetyl-α-D-glucopyranosyl)-β-D-glucopyranosyl]benzamide;

r) N-(2,2',3,3',4,6,6'-hepta-O-acetyl-β-D-maltosyl)-4-butoxy-5-chloro-3-methoxy-benzamide;

s) N[(6-O-benzoyloxy-4',6'-O-benzylidene)-β-D-maltosyl]-4-butoxy-3-chloro-5-methoxy-benzamide or a pharmaceutically acceptable salt thereof;

t) N-[(2,2',3,3'4',6,6'-hepta-O-acetyl-β-D-maltosyl]4-(4-nitrilo-butoxy)-3-nitro-benzamide;

u) N-(4',6'-O-benzylidene-β-D-maltosyl)-4-(4-nitrilo-butoxy)-3-nitro-benzamide or a pharmaceutically acceptable salt thereof;

v) N-(2,2',3,3'-tetra-O-acetyl-6-O-benzoyl-4',6'-O-benzylidene-β-D-maltosyl)-4-(4-nitrilo-butoxy)-3-nitro-benzamide;

w) N-[(2,2',3,3'4',6,6'-hepta-O-acetyl-β-D-maltosyl]-3-amino-4-(4-nitrilo-butoxy)-benzamide;

x) N-[(2,2',3,3'4',6,6'-hepta-O-acetyl-β-D-maltosyl]-6-chloropyridine-3-carboxamide or a pharmaceutically acceptable salt thereof;

y) N-(hepta-O-acetyl-β-D-maltosyl)-2,6-dimethoxy-pyridine-3-carboxamide or a pharmaceutically acceptable salt thereof;

z) N-(hepta-O-acetyl-β-D-maltosyl)-5-bromopyridine-3-carboxamide or a pharmaceutically acceptable salt thereof;

aa) N-(hepta-O-acetyl-β-D-maltosyl)-3-(trifluoromethyl)-benzamide;

bb) N-(4',6'-O-benzylidene-β-D-maltosyl)-3-(trifluoromethyl)-benzamide or a pharmaceutically acceptable salt thereof;

cc) N-[{6-O-benzoyl-4',6'-O-benzylidene}-β-D-maltosyl]-3-(trifluoromethyl)-benzamide or a pharmaceutically acceptable salt thereof;

dd) N-(hepta-O-acetyl-β-D-maltosyl)-6-methylpyridine-3-carboxamide or a pharmaceutically acceptable salt thereof;

ee) N-(2,2',3,3',4,6,6'-hepta-O-acetyl-β-D-maltosyl)-4-butoxy-3,5-dichloro-benzylamide;

ff) N-(4',6'-O-benzylidene-β-D-maltosyl)-4-butoxy-3,5-dichloro-benzamide or a pharmaceutically acceptable salt thereof;

gg) N-(2,2',3,3',4',6,6'-hepta-O-acetyl-β-D-maltosyl)-1-(3,4-dimethoxy)-phenyl-acetamide;
hh) N-(hepta-O-acetyl-β-D-maltosyl)-2(4-hydroxy-3-nitro-phenyl)-acetamide or a pharmaceutically acceptable salt thereof; or
ii) N-(2,2',3,3',4',6,6'-hepta-O-acetyl-β-D-maltosyl)-2-(4-chloro-3-nitro-phenyl)-acetamide.

15. A method of treating or inhibiting hyperproliferative vascular disorders in a mammal in need thereof, which comprises administering to said mammal an effective amount of a compound of formula I having the structure

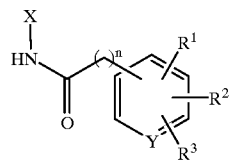

wherein
Y is C or N;
where n is 0–3;
X is

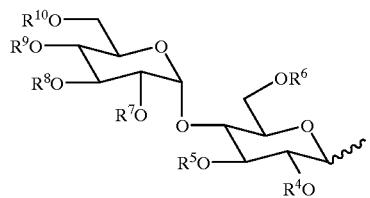

$R^1$, and $R^2$ are each independently, hydrogen, alkyl of 1 to 6 carbon atoms, halo, acetyl, phenyl, $CF_3$, CN, OH, $NO_2$, $NH_2$, alkoxy of 1 to 6 carbon atoms, or cyanoalkoxy of 2 to 7 carbon atoms;

$R^3$ is hydrogen, acylamide of 2 to 6 carbon atoms or alkoxy of 1 to 6 carbon atoms;

$R^4$, $R^5$, $R^6$, $R^7$, and $R^8$ are each, independently, acyl of 1 to 6 carbon atoms, benzyl substituted with $R^1$, and $R^2$; or benzoyl substituted with $R^1$ and $R^2$;

$R^9$ and $R^{10}$ are each, independently, acyl of 1 to 6 carbon atoms, or the $R^9$ and $R^{10}$ groups on the 4' and 6' positions of the maltose may be taken together to form a cyclic acetal which may be substituted with alkyl of 1 to 6 carbon atoms, two alkyl groups each having 1 to 6 carbon atoms, pyridine substituted with $R^1$, phenyl substituted with $R^1$, benzyl substituted with $R^1$, 2-phenylethyl substituted with $R^1$, or 3-phenylpropyl substituted with $R^1$;

with the provisio that when $R^1$ or $R^2$ are cyanoalkoxy of 2–7 carbon atoms, $R^3$ is not acylamide, and further provided that when $R^1$, $R^2$, or $R^3$ are alkoxy of 1–6 carbon atoms, at least one of $R^1$, $R^2$, $R^3$, or $R^4$ are not hydrogen;

or a pharmaceutically acceptable salt thereof.

16. A method of treating or inhibiting restenosis in a mammal in need thereof, which comprises administering to said mammal an effective amount of compound of formula I having the structure

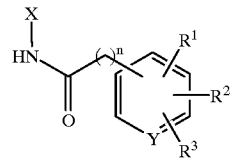

wherein
Y is C or N;
where n is 0–3;
X is

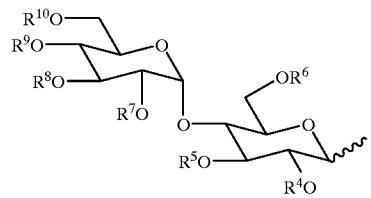

$R^1$, and $R^2$ are each independently, hydrogen, alkyl of 1 to 6 carbon atoms, halo, acetyl, phenyl, $CF_3$, CN, OH, $NO_2$, $NH_2$, alkoxy of 1 to 6 carbon atoms, or cyanoalkoxy of 2 to 7 carbon atoms;

$R^3$ is hydrogen, acylamide of 2 to 6 carbon atoms or alkoxy of 1 to 6 carbon atoms;

$R^4$, $R^5$, $R^6$, $R^7$, and $R^8$ are each, independently, acyl of 1 to 6 carbon atoms, benzyl substituted with $R^1$, and $R^2$; or benzoyl substituted with $R^1$ and $R^2$;

$R^9$ and $R^{10}$ are each, independently, acyl of 1 to 6 carbon atoms, or the $R^9$ and $R^{10}$ groups on the 4' and 6' positions of the maltose may be taken together to form a cyclic acetal which may be substituted with alkyl of 1 to 6 carbon atoms, two alkyl groups each having 1 to 6 carbon atoms, pyridine substituted with $R^1$, phenyl substituted with $R^1$, benzyl substituted with $R^1$, 2-phenylethyl substituted with $R^1$, or 3-phenylpropyl substituted with $R^1$;

with the provisio that when $R^1$ or $R^2$ are cyanoalkoxy of 2–7 carbon atoms, $R^3$ is not acylamide, and further provided that when $R^1$, $R^2$, or $R^3$ are alkoxy of 1–6 carbon atoms, at least one of $R^1$, $R^2$, $R^3$, or $R^4$ are not hydrogen;

or a pharmaceutically acceptable salt thereof.

17. The method according to claim 16, wherein the restenosis results from a vascular angioplasty procedure, vascular reconstructive surgery, or organ or tissue transplantation.

18. A method of inhibiting angiogenesis in a malignant tumor, sarcoma, or neoplastic tissue in a mammal in need thereof, which comprises administering to said mammal an effective amount of a compound of formula I having the structure

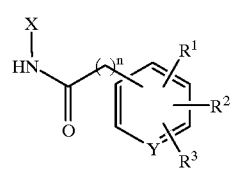

wherein

Y is C or N;

where n is 0–3;

X is

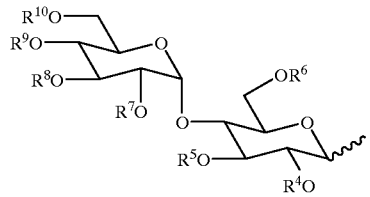

$R^1$, and $R^2$ are each independently, hydrogen, alkyl of 1 to 6 carbon atoms, halo, acetyl, phenyl, $CF_3$, CN, OH, $NO_2$, $NH_2$, alkoxy of 1 to 6 carbon atoms, or cyanoalkoxy of 2 to 7 carbon atoms, $R^3$ is hydrogen, acylamide of 2 to 6 carbon atoms or alkoxy of 1 to 6 carbon atoms;

$R^4$, $R^5$, $R^6$, $R^7$, and $R^8$ are each, independently, acyl of 1 to 6 carbon atoms, benzyl substituted with $R^1$, and $R^2$; or benzoyl substituted with $R^1$ and $R^2$;

$R^9$ and $R^{10}$ are each, independently, acyl of 1 to 6 carbon atoms, or the $R^9$ and $R^{10}$ groups on the 4' and 6' positions of the maltose may be taken together to form a cyclic acetal which may be substituted with alkyl of 1 to 6 carbon atoms, two alkyl groups each having 1 to 6 carbon atoms, pyridine substituted with $R^1$, phenyl substituted with $R^1$, benzyl substituted with $R^1$, 2-phenylethyl substituted with $R^1$, or 3-phenylpropyl substituted with $R^1$;

with the provisio that when $R^1$ or $R^2$ are cyanoalkoxy of 2–7 carbon atoms, $R^3$ is not acylamide, and further provided that when $R^1$, $R^2$, or $R^3$ are alkoxy of 1–6 carbon atoms, at least one of $R^1$, $R^2$, $R^3$, or $R^4$ are not hydrogen;

or a pharmaceutically acceptable salt thereof.

19. A pharmaceutical composition which comprises a compound of formula I having the structure

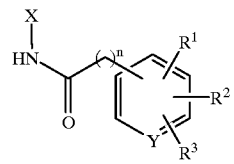

I wherein
Y is C or N;
where n is 0–3;
X is

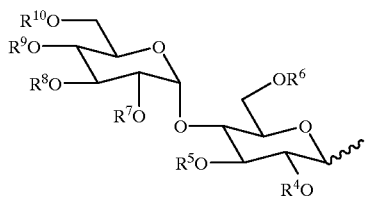

$R^1$, and $R^2$ are each independently, hydrogen, alkyl of 1 to 6 carbon atoms, halo, acetyl, phenyl, $CF_3$, CN, OH, $NO_2$, $NH_2$, alkoxy of 1 to 6 carbon atoms, or cyanoalkoxy of 2 to 7 carbon atoms;

$R^3$ is hydrogen, acylamide of 2 to 6 carbon atoms or alkoxy of 1 to 6 carbon atoms;

$R^4$, $R^5$, $R^6$, $R^7$, and $R^8$ are each, independently, acyl of 1 to 6 carbon atoms, benzyl substituted with $R^1$, and $R^2$; or benzoyl substituted with $R^1$ and $R^2$;

$R^9$ and $R^{10}$ are each, independently, acyl of 1 to 6 carbon atoms, or the $R^9$ and $R^{10}$ groups on the 4' and 6' positions of the maltose may be taken together to form a cyclic acetal which may be substituted with alkyl of 1 to 6 carbon atoms, two alkyl groups each having 1 to 6 carbon atoms, pyridine substituted with $R^1$, phenyl substituted with $R^1$, benzyl substituted with $R^1$, 2-phenylethyl substituted with $R^1$, or 3-phenylpropyl substituted with $R^1$;

with the provisio that when $R^1$ or $R^2$ are cyanoalkoxy of 2–7 carbon atoms, $R^3$ is not acylamide, and further provided that when $R^1$, $R^2$, or $R^3$ are alkoxy of 1–6 carbon atoms, at least one of $R^1$, $R^2$, $R^3$, or $R^4$ are not hydrogen;

or a pharmaceutically acceptable salt thereof, and a pharmaceutical carrier.

* * * * *